US012742142B2

(12) United States Patent
Erickson et al.

(10) Patent No.: US 12,742,142 B2
(45) Date of Patent: Sep. 22, 2026

(54) METHODS AND ARTICLES FOR TESTING DISINFECTANT AND SANITIZER EFFICACY

(71) Applicant: STRATIX LABS CORPORATION, St. Paul, MN (US)

(72) Inventors: Joshua Erickson, Blaine, MN (US); Mark Mulvahill, St. Louis Park, MN (US); Maya Burroughs, St. Paul, MN (US)

(73) Assignee: Stratix Lab Corporation, St. Paul, MN (US)

( * ) Notice: Subject to any disclaimer, the term of this patent is extended or adjusted under 35 U.S.C. 154(b) by 637 days.

(21) Appl. No.: 18/099,598

(22) Filed: Jan. 20, 2023

(65) Prior Publication Data

US 2023/0151404 A1 May 18, 2023

Related U.S. Application Data

(63) Continuation of application No. PCT/US2021/042229, filed on Jul. 19, 2021.

(Continued)

(51) Int. Cl.
*C12M 1/30* (2006.01)
*C12M 1/00* (2006.01)
(Continued)

(52) U.S. Cl.
CPC ............ *C12M 33/02* (2013.01); *C12M 23/38* (2013.01); *C12N 1/20* (2013.01); *C12Q 1/18* (2013.01);

(Continued)

(58) Field of Classification Search
CPC ......... C12M 33/02; C12M 23/38; C12N 1/20; C12Q 1/18; G01N 35/00029
See application file for complete search history.

(56) References Cited

U.S. PATENT DOCUMENTS 3,450,129 A 6/1969 Avery et al.
3,671,400 A 6/1972 Cekoric et al.
(Continued)

FOREIGN PATENT DOCUMENTS

WO 9715331 A1 5/1997

OTHER PUBLICATIONS

Camilleri et al. 2019 J. Bacteriol. vol. 201 (14) 1-19.*
(Continued)

*Primary Examiner* — Manjunath N Rao
(74) *Attorney, Agent, or Firm* — Stinson LLP

(57) ABSTRACT

Methods of evaluating the antimicrobial efficacy of a hard surface disinfectant or sanitizer and test articles are disclosed. An example method may include removing a preserved antimicrobial test article from a sealed container. The preserved antimicrobial test article may comprise a non-water soluble substrate and a thin microbial layer attached to the substrate comprising viable microbial material, a stabilizing mixture, and a residual water content of less than 5.0%. The method may also include contacting the preserved antimicrobial test article with a predetermined amount of the test substance without rehydrating the preserved microbial article and without detaching the layer comprising the viable microbial material from the substrate prior to contact with the test substance.

17 Claims, 7 Drawing Sheets

10

Related U.S. Application Data

(60) Provisional application No. 63/138,636, filed on Jan. 18, 2021, provisional application No. 63/061,784, filed on Aug. 5, 2020, provisional application No. 63/053,800, filed on Jul. 20, 2020.

(51) Int. Cl.
*C12N 1/20* (2026.01)
*C12Q 1/18* (2006.01)
*G01N 35/00* (2006.01)

(52) U.S. Cl.
CPC .................. *G01N 35/00029* (2013.01); *G01N 2035/00099* (2013.01)

(56) References Cited

U.S. PATENT DOCUMENTS

| | | | |
|---|---|---|---|
| 4,175,008 | A | 11/1979 | White |
| 4,311,792 | A | 1/1982 | Avery |
| 4,353,868 | A | 10/1982 | Joslin et al. |
| 4,615,823 | A | 10/1986 | Tokuyama et al. |
| 4,749,655 | A | 6/1988 | Monthony et al. |
| 4,978,504 | A | 12/1990 | Nason |
| 5,078,968 | A | 1/1992 | Nason |
| 5,114,003 | A | 5/1992 | Jackisch et al. |
| 5,155,039 | A | 10/1992 | Chrisope et al. |
| 5,238,649 | A | 8/1993 | Nason |
| 5,266,266 | A | 11/1993 | Nason |
| 5,279,964 | A | 1/1994 | Chrisope |
| 5,733,777 | A | 3/1998 | Dudney |
| 5,856,172 | A | 1/1999 | Greenwood et al. |
| 5,879,635 | A | 3/1999 | Nason |
| 7,186,502 | B2 | 3/2007 | Vesey |
| 7,374,904 | B2 | 5/2008 | Vesey et al. |
| 7,645,608 | B2 | 1/2010 | Greene |
| D655,017 | S | 2/2012 | Mosler et al. |
| D681,230 | S | 4/2013 | Mosler et al. |
| 8,475,404 | B2 | 7/2013 | Foshee et al. |
| 8,821,436 | B2 | 9/2014 | Mosler et al. |
| 8,979,784 | B2 | 3/2015 | Triva |
| 9,011,358 | B2 | 4/2015 | Triva |
| 9,173,779 | B2 | 11/2015 | Triva |
| 9,428,788 | B2 | 8/2016 | Triva |
| D769,444 | S | 10/2016 | Mosler et al. |
| 9,504,452 | B2 | 11/2016 | Triva |
| 10,092,275 | B2 | 10/2018 | Triva |
| 10,327,741 | B2 | 6/2019 | Triva |
| 10,610,343 | B2 | 4/2020 | Stroud |
| 2006/0040340 | A1 | 2/2006 | Greene |
| 2011/0087164 | A1 | 4/2011 | Mosler et al. |
| 2014/0106445 | A1 | 4/2014 | Triva |
| 2015/0282916 | A1 | 10/2015 | Stroud |
| 2017/0094986 | A1 | 4/2017 | Brocheret et al. |
| 2022/0081701 | A1 | 3/2022 | Erickson et al. |

OTHER PUBLICATIONS

Tomasino et al. Journal of AOAC International, 2008 vol. 91 (4)-833-840.*

Krasucka et al., "Karl Fisher determination of residual moisture in veterinary vaccines—practical implementation in market monitoring," Acta Pol. Pharm. 69: 1364-1367, 2012.

May et al., "The gravimetric method for the determination of residual moisture in freeze-dried biological products," Cryobiology 26: 277-284, 1989 [Abstract Only].

Reh et al., "Determination of water content in powdered milk," Food Chem. 86: 457-464, 2004. [Abstract Only].

Zheng et al., "Determination of moisture content of lyophilized allergen vaccines by NIR spectroscopy," J. Pharm. Biomed. Anal. 46: 592-596, 2008.

* cited by examiner

METHODS AND ARTICLES FOR TESTING DISINFECTANT AND SANITIZER EFFICACY

CROSS-REFERENCE TO RELATED APPLICATIONS

This application is a continuation of International Application No. PCT/US2021/042229, filed Jul. 19, 2021, which claims priority to U.S. Provisional Application No. 63/053,800, filed on Jul. 20, 2020, claims priority to U.S. Provisional Application No. 63/061,784, filed on Aug. 5, 2020, and claims priority to U.S. Provisional Application No. 63/138,636, filed on Jan. 18, 2021, the entirety of which are incorporated herein by reference.

TECHNICAL FIELD

The present disclosure pertains to microbiology. More particularly, the present disclosure pertains to methods and articles for evaluating the antimicrobial efficacy of a test sample/substance (e.g., a disinfectant or a sanitizer) against microorganisms and virions attached to an inanimate surface.

BACKGROUND

Pathogenic microorganisms can have economic, health, and safety impacts.

SUMMARY

Disclosed herein are methods of evaluating the antimicrobial efficacy of a test substance (e.g., a hard surface disinfectant or sanitizer) that include: providing a test substance suspected of antimicrobial efficacy, providing a preserved antimicrobial test article, removing the preserved antimicrobial test article from a sealed container, contacting the preserved antimicrobial test article with a predetermined amount of the test substance without rehydrating the preserved microbial article and without detaching the layer comprising the viable microbial material from the substrate prior to contact with the test substance, maintaining contact between the antimicrobial test article and the test substance for a predetermined test contact time, contacting the antimicrobial test article and the test substance with a neutralizer after the test contact time, agitating the antimicrobial test article and observing an indication of antimicrobial efficacy, where: the preserved antimicrobial test article comprises a non-water soluble substrate, a thin microbial layer attached to the substrate comprising viable microbial material, a stabilizing mixture, and a residual water content of less than 5.0%, where: the viable microbial material comprises between 3.0 logs to 9.0 logs of viable microbial material that has a loss of viability of less than 0.5 log over at least 30 days at 4° C., where: the article is sealed in a container, and where the article is used in evaluating the antimicrobial efficacy of the test substance (i) directly from the preserved state without rehydration and (ii) without detaching the layer comprising the viable microbial material from the substrate prior to contact with a test substance. In some embodiments of these methods, the viable microbial material includes bacterial cells. In some embodiments, the bacterial cells include *Pseudomonas aeruginosa* ATCC® 15442™ or *Staphylococcus aureus* ATCC® 6538™. In some examples of these methods, the viable microbial material includes fungal cells. In some examples of these methods, the viable microbial material includes virions.

In some embodiments, the non-water soluble substrate is a disc, a rectangle, or a cylinder. In some embodiments, the substrate has a flat side with a surface area between 10 $mm^2$ to 10,000 $mm^2$. In some embodiments, the thin microbial layer is attached to the flat side of the substrate. In some embodiments, the non-water soluble substrate comprises a porous or a non-porous material. In some examples, the non-water soluble substrate comprises a non-porous material selected from the following group: metal, steel, glass, and plastic. In some examples, the non-water soluble substrate comprises a porous material selected from the following group: ceramic or wood. In some embodiments of these methods, the non-water soluble substrate is a stainless steel disc with a diameter between about 3 mm to about 25 mm and a thickness between about 1 mm and about 10 mm. In some embodiments of these methods, the non-water soluble substrate is a borosilicate glass disc with a diameter between about 3 mm to about 25 mm. In some embodiments of these methods, the non-water soluble substrate is a borosilicate glass rectangle with a length between about 5 mm to about 100 mm, a width between about 5 mm to about 100 mm, and a thickness between about 1 mm to about 5 mm.

In some examples of these methods, the stabilizing mixture includes a sugar. In some examples, the sugar is a non-reducing sugar. In some examples, the stabilizing mixture includes sucrose. In some examples, the stabilizing mixture includes an antioxidant. In some examples, the stabilizing mixture includes ascorbic acid. In some examples, the stabilizing mixture includes a buffer. In some examples, the stabilizing mixture includes Tris(hydroxymethyl)aminomethane. In some examples, the stabilizing mixture includes a growth nutrient. In some examples, the stabilizing mixture includes synthetic broth. In some examples, the stabilizing mixture comprises between 5.0% to 15% of a sugar, between 2.0% to 10% of an antioxidant, and synthetic broth. In some examples, the thin microbial layer further comprises a soil load. In some examples, the soil load is between 1% to 15% by weight. In some examples, the soil load comprises an organic salt. In some examples, the soil load comprises bovine serum. In some examples, the thin microbial layer has a residual water content of less than 4% by weight. In some examples, the thin microbial layer has a residual water content of less than 3% by weight. In some examples, the thin microbial layer has a residual water content of less than 2% by weight.

In some examples, the viable microbial material has a loss of viability of less than about 0.5 log over a period of 30 days at a temperature of 4° C. In some examples, the viable microbial material has a loss of viability of less than about 0.5 log over a period of 90 days at a temperature of 4° C. In some examples, the viable microbial material has a loss of viability of less than about 0.5 log over a period of 180 days at a temperature of 4° C. In some examples, the viable microbial material has a loss of viability of less than about 0.5 log over a period of 365 days at a temperature of 4° C. In some examples, the viable microbial material has a loss of viability of less than about 0.3 log over a period of 90 days at a temperature of 4° C. In some examples, the viable microbial material has a loss of viability of less than about 0.1 log over a period of 90 days at a temperature of 4° C. In some embodiments of these methods, the article is disposed within a primary container and the primary container is sealed within a secondary container that has low permeability to moisture and oxygen. In some embodiments, the primary container, the secondary container, or both are impermeable to at least one of moisture and oxygen. In some embodiments, a desiccant is disposed within the secondary container. In some embodiments, an oxygen scavenger is disposed within the secondary container.

In some embodiments of these methods, observing an indication of antimicrobial efficacy includes quantitative assessment. In some embodiments, quantitative assessment includes determining a loss of viable cells. In some embodiments, quantitative assessment includes utilizing a stain or a dye. In some embodiments, observing an indication of antimicrobial efficacy includes qualitative assessment. In some embodiments, the test substance includes a surface disinfectant or a sanitizer. In some embodiments, the test contact time is between 30 seconds to 10 minutes.

Also provided herein are preserved antimicrobial test articles for evaluating the antimicrobial efficacy of a test substance (e.g., a surface disinfectant or sanitizer) that include: a non-water soluble substrate, a thin microbial layer attached to the substrate comprising viable microbial material, a stabilizing mixture, and a residual water content of less than 5.0%, wherein the thin microbial layer comprises between 3.0 log to 9.0 log of viable microbial material, wherein the viable microbial material has a loss of viability of less than 0.5 log over at least 30 days at 4° C., wherein the article is sealed in a container, wherein the article is used in evaluating the antimicrobial efficacy of a hard surface disinfectant or sanitizer (i) directly from the preserved state without rehydration and (ii) without detaching the layer comprising the viable microbial material from the substrate prior to contact with a test substance.

Also provided are methods of manufacturing a preserved antimicrobial test article for evaluating the antimicrobial efficacy of a hard surface disinfectant or sanitizer that include: suspending a pellet of viable microbial material in a predetermined amount of a solution comprising a stabilizing mixture to create a suspension with a predetermined amount of viable microbial material per volume, agitating the suspension until the viable microbial material and stabilizing mixture are homogenously dispersed throughout the suspension, depositing a predetermined amount of the suspension onto a non-water soluble substrate to create an antimicrobial test article comprising a thin layer of the homogenous suspension attached to the article, sealing the antimicrobial test article in a container, where: the viable microbial material has a loss of viability of less than 0.5 log over at least 30 days at 4° C., where: the article is used in evaluating the antimicrobial efficacy of a hard surface disinfectant or sanitizer (i) directly from the preserved state without rehydration and (ii) without detaching the layer comprising the viable microbial material from the substrate prior to contact with a test substance. In some embodiments, the article is disposed within a primary container and the primary container is sealed within a secondary container that has low permeability to moisture and oxygen. In some embodiments, the primary container, the secondary container, or both are impermeable to moisture and oxygen. In some embodiments, a desiccant is disposed within the secondary container. In some embodiments, an oxygen scavenger is disposed within the secondary container. In some embodiments, the concentrated pellet is prepared by centrifuging a suspension of viable microbial cells with a concentration between $1.0\times10^4$ and $1\times10^9$ per mL. In some embodiments, the stabilizing mixture comprises a sugar. In some embodiments, the sugar is a non-reducing sugar. In some embodiments, the stabilizing mixture further comprises an antioxidant. In some embodiments, the stabilizing mixture comprises a growth nutrient. In some embodiments, the stabilizing mixture comprises a buffer. In some embodiments, the stabilizing mixture comprises between 1% and 15% of a sugar, between 1% and 15% of an antioxidant, and one or both of a growth nutrient and a buffer. In some embodiments, the stabilizing mixture comprises between 5% and 15% of a sugar, between 2% and 10% of an antioxidant, and one or both of a growth nutrient and a buffer. In some embodiments, the stabilizing mixture further comprises a soil load. In some embodiments, the soil load is between 1% to 15% by weight. In some embodiments, the soil load comprises an organic salt. In some embodiments, the soil load comprises bovine serum. In some embodiments, the stabilizing mixture comprises a pH of between 6.4 and 8.4. In some embodiments, the stabilizing mixture comprises a pH of between 6.9 and 7.9. In some embodiments, the stabilizing mixture comprises a pH of between 7.2 and 7.6. In some embodiments, the stabilizing mixture comprises a pH of 7.4. In some embodiments, after resuspension the viable microbial material has a concentration between $1.0\times10^4$ and $1\times10^9$ CFU per mL. In some embodiments, after resuspension the viable microbial material has been concentrated by a factor of between 2 and 10. In some embodiments, after resuspension the viable microbial material has been concentrated by a factor of between 4 and 10. In some embodiments, after resuspension the viable microbial material has been concentrated by a factor of between 4 and 6. In some embodiments, a volume of between 5 μL and 30 μL of the suspension is deposited onto the non-water soluble substrate to create the thin microbial layer. In some embodiments, the method further comprises freezing and lyophilizing the antimicrobial test article.

A method of evaluating the antimicrobial efficacy of a hard surface disinfectant or sanitizer is disclosed. The method comprises: providing, a test substance suspected of antimicrobial efficacy; a preserved antimicrobial test article comprising: a non-water soluble substrate, a thin microbial layer attached to the substrate comprising viable microbial material, a stabilizing mixture, and a residual water content of less than 5.0%, wherein the viable microbial material comprises between 3.0 logs to 9.0 logs of viable microbial material, wherein the viable microbial material has a loss of viability of less than 0.5 log over at least 30 days at 4° C., wherein the article is sealed in a container, wherein the article is used in evaluating the antimicrobial efficacy of a hard surface disinfectant or sanitizer (i) directly from the preserved state without rehydration and (ii) without detaching the layer comprising the viable microbial material from the substrate prior to contact with a test substance; removing the preserved antimicrobial test article from the sealed container; contacting the preserved antimicrobial test article with a predetermined amount of the test substance without rehydrating the preserved microbial article and without detaching the layer comprising the viable microbial material from the substrate prior to contact with the test substance; maintaining contact between the antimicrobial test article and the test substance for a predetermined test contact time; contacting the antimicrobial test article and the test substance with a neutralizer after the test contact time; agitating the antimicrobial test article; and observing an indication of antimicrobial efficacy.

A method of evaluating the antimicrobial efficacy of a hard surface disinfectant or sanitizer is disclosed. The method comprises: removing a preserved antimicrobial test article from a sealed container, the preserved antimicrobial test article comprising: a non-water soluble substrate, a thin microbial layer attached to the substrate comprising viable microbial material, a stabilizing mixture, and a residual water content of less than 5.0%, wherein the viable microbial material comprises between 3.0 logs to 9.0 logs of viable microbial material, wherein the viable microbial material has a loss of viability of less than 0.5 log over at least 30 days at 4° C., and wherein the article is used in evaluating the antimicrobial efficacy of a hard surface disinfectant or sanitizer (i) directly from the preserved state without rehydration and (ii) without detaching the layer comprising the viable microbial material from the substrate prior to contact with a test substance; contacting the preserved antimicrobial test article with a predetermined amount of the test substance without rehydrating the preserved microbial article and without detaching the layer comprising the viable microbial material from the substrate prior to contact with the test substance; maintaining contact between the antimicrobial test article and the test substance for a predetermined test contact time; contacting the antimicrobial test article and the test substance with a neutralizer after the test contact time; agitating the antimicrobial test article; and observing an indication of antimicrobial efficacy.

Alternatively or additionally to any of the embodiments above, the viable microbial material includes bacterial cells, fungal cells, or virions.

Alternatively or additionally to any of the embodiments above, the bacterial cells include *Pseudomonas aeruginosa* ATCC® 15442™ or *Staphylococcus aureus* ATCC® 6538™.

Alternatively or additionally to any of the embodiments above, the non-water soluble substrate is a disc, a rectangle, or a cylinder.

Alternatively or additionally to any of the embodiments above, the substrate has a flat side with a surface area between 10 $mm^2$ to 10,000 $mm^2$.

Alternatively or additionally to any of the embodiments above, the thin microbial layer is attached to the flat side of the substrate.

Alternatively or additionally to any of the embodiments above, the non-water soluble substrate comprises a porous or a non-porous material.

Alternatively or additionally to any of the embodiments above, the non-water soluble substrate comprises a non-porous material selected from the following group: metal, steel, glass, and plastic.

Alternatively or additionally to any of the embodiments above, the non-water soluble substrate comprises a porous material selected from the following group: ceramic or wood.

Alternatively or additionally to any of the embodiments above, the non-water soluble substrate is a stainless steel disc with a diameter between about 3 mm to about 25 mm and a thickness between about 1 mm and about 10 mm.

Alternatively or additionally to any of the embodiments above, the non-water soluble substrate is a borosilicate glass disc with a diameter between about 3 mm to about 25 mm.

Alternatively or additionally to any of the embodiments above, the non-water soluble substrate is a borosilicate glass rectangle with a length between about 5 mm to about 100 mm, a width between about 5 mm to about 100 mm, and a thickness between about 1 mm to about 5 mm.

Alternatively or additionally to any of the embodiments above, the stabilizing mixture includes a sugar.

Alternatively or additionally to any of the embodiments above, the sugar is a non-reducing sugar.

Alternatively or additionally to any of the embodiments above, the stabilizing mixture includes sucrose.

Alternatively or additionally to any of the embodiments above, the stabilizing mixture includes an antioxidant.

Alternatively or additionally to any of the embodiments above, the stabilizing mixture includes ascorbic acid.

Alternatively or additionally to any of the embodiments above, the stabilizing mixture includes a buffer.

Alternatively or additionally to any of the embodiments above, the stabilizing mixture includes Tris(hydroxymethyl) aminomethane.

Alternatively or additionally to any of the embodiments above, the stabilizing mixture includes a growth nutrient.

Alternatively or additionally to any of the embodiments above, the stabilizing mixture includes synthetic broth.

Alternatively or additionally to any of the embodiments above, the stabilizing mixture comprises between 5.0% to 15% of a sugar, between 2.0% to 10% of an antioxidant, and synthetic broth.

Alternatively or additionally to any of the embodiments above, the thin microbial layer further comprises a soil load.

Alternatively or additionally to any of the embodiments above, the soil load is between 1% to 15% by weight.

Alternatively or additionally to any of the embodiments above, the soil load comprises an organic salt.

Alternatively or additionally to any of the embodiments above, the soil load comprises bovine serum.

Alternatively or additionally to any of the embodiments above, the thin microbial layer has a residual water content of less than 4% by weight.

Alternatively or additionally to any of the embodiments above, the thin microbial layer has a residual water content of less than 3% by weight.

Alternatively or additionally to any of the embodiments above, the thin microbial layer has a residual water content of less than 2% by weight.

Alternatively or additionally to any of the embodiments above, the viable microbial material has a loss of viability of less than about 0.5 log over a period of 30 days at a temperature of 4° C.

Alternatively or additionally to any of the embodiments above, the viable microbial material has a loss of viability of less than about 0.5 log over a period of 90 days at a temperature of 4° C.

Alternatively or additionally to any of the embodiments above, the viable microbial material has a loss of viability of less than about 0.5 log over a period of 180 days at a temperature of 4° C.

Alternatively or additionally to any of the embodiments above, the viable microbial material has a loss of viability of less than about 0.5 log over a period of 365 days at a temperature of 4° C.

Alternatively or additionally to any of the embodiments above, the viable microbial material has a loss of viability of less than about 0.3 log over a period of 90 days at a temperature of 4° C.

Alternatively or additionally to any of the embodiments above, the viable microbial material has a loss of viability of less than about 0.1 log over a period of 90 days at a temperature of 4° C.

Alternatively or additionally to any of the embodiments above, the article is disposed within a primary container and the primary container is sealed within a secondary container that has low permeability to moisture and oxygen.

Alternatively or additionally to any of the embodiments above, the primary container, the secondary container, or both are impermeable to at least one of moisture and oxygen.

Alternatively or additionally to any of the embodiments above, a desiccant is disposed within the secondary container.

Alternatively or additionally to any of the embodiments above, an oxygen scavenger is disposed within the secondary container.

Alternatively or additionally to any of the embodiments above, observing an indication of antimicrobial efficacy includes quantitative assessment.

Alternatively or additionally to any of the embodiments above, quantitative assessment includes determining a loss of viable cells.

Alternatively or additionally to any of the embodiments above, quantitative assessment includes utilizing a stain or a dye.

Alternatively or additionally to any of the embodiments above, observing an indication of antimicrobial efficacy includes qualitative assessment.

Alternatively or additionally to any of the embodiments above, the test substance includes a hard surface disinfectant or a sanitizer.

Alternatively or additionally to any of the embodiments above, the test contact time is between 30 seconds to 10 minutes.

A method of evaluating the antimicrobial efficacy of a hard surface disinfectant or sanitizer is disclosed. The method comprises: removing a preserved antimicrobial test article from a sealed container, the preserved antimicrobial test article comprising: a non-water soluble substrate, a thin microbial layer attached to the substrate comprising viable microbial material, a stabilizing mixture, and a residual water content of less than 5.0%, wherein the viable microbial material comprises between 3.0 logs to 9.0 logs of viable microbial material, wherein the viable microbial material has a loss of viability of less than 0.5 log over at least 30 days at 4° C., and wherein the article is used in evaluating the antimicrobial efficacy of a hard surface disinfectant or sanitizer (i) directly from the preserved state without rehydration and (ii) without detaching the layer comprising the viable microbial material from the substrate prior to contact with a test substance; contacting the preserved antimicrobial test article with a predetermined amount of the test substance without rehydrating the preserved microbial article and without detaching the layer comprising the viable microbial material from the substrate prior to contact with the test substance; maintaining contact between the antimicrobial test article and the test substance for a predetermined test contact time; contacting the antimicrobial test article and the test substance with a neutralizer after the test contact time; agitating the antimicrobial test article; and observing an indication of antimicrobial efficacy.

Alternatively or additionally to any of the embodiments above, observing an indication of antimicrobial efficacy includes quantitative assessment.

Alternatively or additionally to any of the embodiments above, quantitative assessment includes determining a loss of viable cells.

Alternatively or additionally to any of the embodiments above, quantitative assessment includes utilizing a stain or a dye.

Alternatively or additionally to any of the embodiments above, observing an indication of antimicrobial efficacy includes qualitative assessment.

A test article is disclosed. The test article comprises: a container; a preserved antimicrobial test article sealed within the container, the preserved antimicrobial test article comprising: a non-water soluble substrate, a thin microbial layer attached to the substrate comprising viable microbial material, a stabilizing mixture, and a residual water content of less than 5.0%, wherein the viable microbial material comprises between 3.0 logs to 9.0 logs of viable microbial material, wherein the viable microbial material has a loss of viability of less than 0.5 log over at least 30 days at 4° C., and wherein the article is used in evaluating the antimicrobial efficacy of a hard surface disinfectant or sanitizer (i) directly from the preserved state without rehydration and (ii) without detaching the layer comprising the viable microbial material from the substrate prior to contact with a test substance.

Alternatively or additionally to any of the embodiments above, the viable microbial material includes bacterial cells, fungal cells, or virions.

Alternatively or additionally to any of the embodiments above, the non-water soluble substrate is a disc, a rectangle, or a cylinder.

Alternatively or additionally to any of the embodiments above, the substrate has a flat side with a surface area between 10 $mm^2$ to 10,000 $mm^2$.

Alternatively or additionally to any of the embodiments above, the thin microbial layer is attached to the flat side of the substrate.

Alternatively or additionally to any of the embodiments above, the non-water soluble substrate comprises a porous or a non-porous material.

Alternatively or additionally to any of the embodiments above, the stabilizing mixture includes a sugar.

Alternatively or additionally to any of the embodiments above, the stabilizing mixture includes an antioxidant.

Alternatively or additionally to any of the embodiments above, the stabilizing mixture includes a growth nutrient.

Alternatively or additionally to any of the embodiments above, the article is disposed within a primary container and the primary container is sealed within a secondary container that has low permeability to moisture and oxygen.

A method of evaluating the antimicrobial efficacy of a surface disinfectant or sanitizer is disclosed. The method comprises: removing a preserved antimicrobial test article from a sealed container, the preserved antimicrobial test article comprising: a non-water soluble substrate, a thin microbial layer attached to the substrate comprising viable microbial material, a stabilizing mixture, and a residual water content of less than 5.0%, wherein the viable microbial material comprises between 3.0 logs to 9.0 logs of viable microbial material, wherein the viable microbial material has a loss of viability of less than 0.5 log over at least 30 days at 4° C., and wherein the article is used in evaluating the antimicrobial efficacy of a surface disinfectant or sanitizer (i) directly from the preserved state without rehydration and (ii) without detaching the layer comprising the viable microbial material from the substrate prior to contact with a test sample; contacting the preserved antimicrobial test article with the test sample without rehydrating the preserved microbial article and without detaching the layer comprising the viable microbial material from the substrate prior to contact with the test sample; maintaining contact between the antimicrobial test article and the test sample for a predetermined test contact time; and observing an indication of antimicrobial efficacy.

Alternatively or additionally to any of the embodiments above, observing an indication of antimicrobial efficacy includes quantitative assessment.

Alternatively or additionally to any of the embodiments above, quantitative assessment includes determining a loss of viable cells.

Alternatively or additionally to any of the embodiments above, quantitative assessment includes utilizing a stain or a dye.

Alternatively or additionally to any of the embodiments above, observing an indication of antimicrobial efficacy includes qualitative assessment.

A test article is disclosed. The test article comprises: a container; a preserved antimicrobial test article sealed within the container, the preserved antimicrobial test article comprising: a non-water soluble substrate, a thin microbial layer attached to the substrate comprising viable microbial material, a stabilizing mixture, and a residual water content of less than 5.0%, wherein the viable microbial material comprises between 3.0 logs to 9.0 logs of viable microbial material, wherein the viable microbial material has a loss of viability of less than 0.5 log over at least 30 days at 4° C., and wherein the article is used in evaluating the antimicrobial efficacy of a surface disinfectant or sanitizer (i) directly from the preserved state without rehydration and (ii) without detaching the layer comprising the viable microbial material from the substrate prior to contact with a test sample.

Alternatively or additionally to any of the embodiments above, the viable microbial material includes bacterial cells, fungal cells, or virions.

Alternatively or additionally to any of the embodiments above, the non-water soluble substrate is a disc, a rectangle, or a cylinder.

Alternatively or additionally to any of the embodiments above, the substrate has a flat side with a surface area between 10 $mm^2$ to 10,000 $mm^2$.

Alternatively or additionally to any of the embodiments above, the thin microbial layer is attached to the flat side of the substrate.

Alternatively or additionally to any of the embodiments above, the non-water soluble substrate comprises a porous or a non-porous material.

Alternatively or additionally to any of the embodiments above, the stabilizing mixture includes a sugar.

Alternatively or additionally to any of the embodiments above, the stabilizing mixture includes an antioxidant.

Alternatively or additionally to any of the embodiments above, the stabilizing mixture includes a growth nutrient.

Alternatively or additionally to any of the embodiments above, the article is disposed within a primary container and the primary container is sealed within a secondary container that has low permeability to moisture and oxygen.

Unless otherwise defined, all technical and scientific terms used herein have the same meaning as commonly understood by one of ordinary skill in the art to which this disclosure belongs. Methods and materials are described herein for use in the present disclosure; other, suitable methods and materials can also be used. The materials, methods, and examples are illustrative only and not intended to be limiting.

All publications, patent applications, patents, sequences, database entries, journal articles, and other references mentioned herein are expressly incorporated by reference in their entirety.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
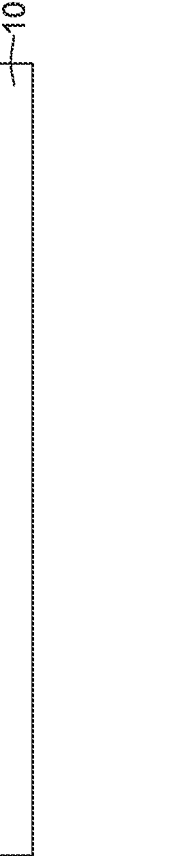
FIG. 1 schematically depicts an example substrate.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure provides methods and articles for evaluating the antimicrobial efficacy of a test sample (e.g., a test substance or other item that is to be tested for antimicrobial efficacy) against a layer of viable microbial material secured to a hard surface. The articles described herein provide a preserved antimicrobial test article that comprises a layer of preserved, viable microbial material secured to a non-water soluble surface and is capable of immediate use in disinfectant efficacy testing.

The current standard methods for evaluating disinfectant performance require testing antimicrobial efficacy of the disinfectant formulation against microbes attached to a hard, inanimate surface. Currently, preparation of inoculated test articles for disinfectant testing is time-consuming, resource-intensive, and prone to error and variability issues. Furthermore, the current state of the art requires that inoculated test articles be used within a short time frame (e.g., less than two hours) before degradation of microbial viability. These issues contribute to standardization problems and hinder the development of disinfectants.

It is accordingly an object of the present disclosure to provide methods and articles that can significantly reduce the complexities and difficulties in evaluating antimicrobial efficacy of disinfectants against a layer of viable microbial material attached to an inanimate surface, and also provide for surface-associated test articles with extensive stability and preservation of integrity and function upon testing. It is another object of the present disclosure to provide methods of manufacturing preserved antimicrobial test articles for evaluating the antimicrobial efficacy of a test sample/substance that are rapid and require a minimal amount of time to produce preserved test articles with the required properties for use.

Still further objects and advantages will become apparent from consideration of the ensuing description.

As can be appreciated in the art, the various aspects described below can be used in combination without limitation.

Preserved Antimicrobial Test Articles

Figure 2:
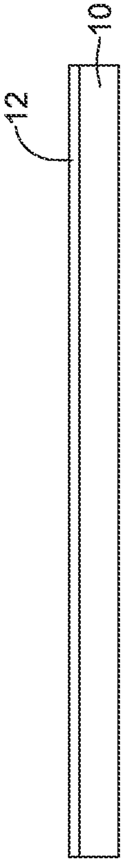
FIG. 2 schematically depicts an example substrate with a layer of microbial material disposed thereon.

Provided herein are preserved antimicrobial test articles for evaluating the antimicrobial efficacy of a test sample/substance. In some instances, the preserved antimicrobial test articles are used for evaluating the antimicrobial efficacy of hard surface antimicrobial agents (e.g., a hard surface disinfectant or sanitizer). The preserved antimicrobial test articles provided herein comprise a non-water soluble substrate and a thin layer attached to the substrate comprising viable microbial material. For example, FIG. 1 depicts an example substrate 10 and FIG. 2 depicts the substrate with a layer of microbial material 12 disposed thereon. In some examples, the thin layer attached to the substrate comprising viable microbial material further comprises a stabilizing mixture. In some examples, the preserved antimicrobial test article comprises a residual water content or residual moisture content. In any of the preserved antimicrobial test articles provided herein, the article retains a required minimum quantity of viable microbial material over a significant period of time. In some examples, the preserved antimicrobial test article is used to evaluate the antimicrobial efficacy of a test sample/substance (i) directly from the preserved state without rehydration and (ii) without detaching the layer comprising viable microbial from the substrate prior to contact with the test sample/substance.

In some examples, the preserved antimicrobial test articles provided herein can comprise a non-water soluble substrate, a thin microbial layer attached to the substrate comprising viable microbial material, a stabilizing mixture, and a residual water content (e.g., a residual water content of less than 10.0%), wherein the thin microbial layer comprises between 3.0 log to 9.0 log of viable microbial material, wherein the viable microbial material has a loss of viability of less than 0.5 log over at least 30 days at 4° C., wherein the article is sealed in a container, and wherein the article is used in evaluating the antimicrobial efficacy of a test sample/substance (e.g., a hard surface disinfectant or sanitizer) (i) directly from the preserved state without rehydration and (ii) without detaching the layer comprising viable microbial material from the substrate prior to contact with the test sample/substance.

The non-water soluble substrate can be made of a porous or non-porous material. Non-limited examples of substrates that can be included in any of the methods or articles herein are described below. The viable microbial material in any of the methods or articles described herein can include bacterial cells, fungal cells, or virions. Non-limiting examples of viable microbial material that can be included in any of the methods or articles herein are described below. The stabilizing mixture can comprise one or more stabilizing agents. Non-limiting examples of stabilizing agents that can be included in any of the methods or articles herein are described below. The thin microbial layer in any of the methods or articles described herein can include a residual water content. Non-limiting examples of the water content that can be included in any of the methods or articles provided herein are described below. Non-limiting examples of the stability that can be included in any of the methods or articles provided herein are described below.

The thin microbial layer included in any of the methods or articles provided herein can be further characterized by its dimensions, surface area, and attachment strength.

In any of the methods or articles provided herein, the preserved antimicrobial test article retains a required minimum quantity of viable microbial material for a minimum period of time after the article's date of manufacture. In some examples, the preserved antimicrobial test article retains at least 3 logs (e.g., at least 3.1 logs, at least 3.2 logs, at least 3.3 logs, at least 3.4 logs, at least 3.5 logs, at least 3.6 logs, at least 3.7 logs, at least 3.8 logs, at least 3.9 logs, at least 4.0 logs, at least 4.1 logs, at least 4.2 logs, at least 4.3 logs, at least 4.4 logs, at least 4.5 logs, at least 4.6 logs, at least 4.7 logs, at least 4.8 logs, at least 4.9 logs, at least 5.0 logs, at least 5.1 logs, at least 5.2 logs, at least 5.3 logs, at least 5.4 logs, at least 5.5 logs, at least 5.6 logs, at least 5.7 logs, at least 5.8 logs, at least 5.9 logs, at least 6.0 logs, at least 6.1 logs, at least 6.2 logs, at least 6.3 logs, at least 6.4 logs, at least 6.5 logs, at least 6.6 logs, at least 6.7 logs, at least 6.8 logs, at least 6.9 logs, at least 7.0 logs, at least 7.1 logs, at least 7.2 logs, at least 7.3 logs, at least 7.4 logs, at least 7.5 logs, at least 7.6 logs, at least 7.7 logs, at least 7.8 logs, at least 7.9 logs, at least 8.0 logs, at least 8.1 logs, at least 8.2 logs, at least 8.3 logs, at least 8.4 logs, at least 8.5 logs, at least 8.6 logs, at least 8.7 logs, at least 8.8 logs, at least 8.9 logs, at least 9.0 logs, at least 9.1 logs, at least 9.2 logs, at least 9.3 logs, at least 9.4 logs, or at least 9.5 logs) of viable microbial material for a minimum period of time after the article's date of manufacture. In some examples, the minimum period of time after the article's date of manufacture is at least 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 35 days, 40 days, 45 days, 50 days, 55 days, 60 days, 65 days, 70 days, 75 days, 80 days, 85 days, 90 days, 120 days, 150 days, 180 days, 210 days, 240 days, 270 days, 300 days, 330 days, 360 days, or 365 days. In some examples, the minimum period of time after the article's date of manufacture is greater than 365 days.

Figure 3:
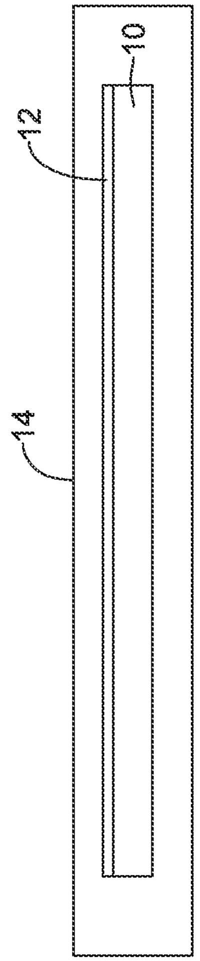
FIG. 3 schematically depicts an example substrate with a layer of microbial material disposed thereon disposed in a container.

The substrate 10 having the layer of microbial material 12 disposed thereon may be disposed in a container or package 14 as shown in FIG. 3. In some instances, the substrate 10 having the layer of microbial material 12 in a primary package or container 14 and a second package or container 16 FIG. 4.

Viable Microbial Material

In any of the methods or articles provided herein, the viable microbial material can be a prokaryotic organism, a eukaryotic organism, a virus, or a virion. Non-limiting examples of the types of microbial material that can be included in any of the methods or articles provided herein include: bacteria, fungi, algae, protist, diatom, archaea, cyanobacteria, virus, and virion. In some embodiments, the viable microbial material can comprise a single type of microbial material, at least two types of microbial material, at least three types of microbial material, at least four types of microbial material, at least five types of microbial material, or more than five types of microbial material.

In some embodiments of the methods or articles provided herein, the viable microbial material can comprise a homogenous population of identical cells or virions. In some embodiments, the viable microbial material can comprise a heterogeneous population of microbial cells or virions. In some embodiments, the viable microbial material in any of the methods or articles provided herein can comprise one organism, at least two different organisms, at least three different organisms, at least four different organisms, at least five different organisms, at least six different organisms, at least seven different organisms, at least eight different organisms, at least nine different organisms, at least ten different organisms, at least twenty different organisms, at least thirty different organisms, or more than thirty different organisms.

In some embodiments, the viable microbial material can comprise one species, at least two species, at least three species, at least four species, at least five species, at least six species, at least seven species, at least eight species, at least nine species, at least ten species, or more than ten species of microorganisms or virions. In some embodiments, the viable microbial material can comprise one strain, at least two strains, at least three strains, at least four strains, at least five strains, at least six strains, at least seven strains, at least eight strains, at least nine strains, at least ten strains, at least fifteen strains, at least twenty strains, at least twenty-five strains, at least thirty strains, at least thirty-five strains, at least forty strains, at least forty-five strains, at least fifty strains, or more than fifty strains of microorganisms or virions. In some examples, the viable microbial material is a gram-positive bacteria or a gram-negative bacteria. In some examples, the viable microbial material is a fungi (e.g., a yeast). In some examples, the viable microbial material is a spore. In some some examples, the viable microbial material is a virion. In some embodiments, the viable microbial material is a microbe selected from the group of: *Acetobacter* spp., *Acetonema* spp., *Acidithiobacillus* spp., *Acinetobacter* spp., *Actinomyces* spp., *Agrobacterium* spp., *Alkalibacillus* spp., *Ammoniphilus* spp., *Amphibacillus* spp., *Anaerobacter* spp., *Anaerospora* spp., *Anaplasma* spp., *Aneurinibacillus* spp., *Anoxybacillus* spp., *Arthrobacter* spp., *Aspergillus* spp., *Aureobasidium* spp., *Azorhizobium* spp., *Azotobacter* spp., *Bacillus* spp., *Bacteroides* spp., *Bartonella* spp., *Beggiatoa* spp., *Bifidobacterium* spp., *Brevibacterium* spp., *Brevibacillus* spp., *Bordetella* spp., *Borrelia* spp., *Brucella* spp., *Burkholderia* spp., *Caldanaerobacter* spp., *Caloramator* spp., *Calymmatobacterium* spp., *Caminicella* spp., *Campylobacter* spp., *Candida* spp., *Cerasibacillus* spp., *Chlamydia* spp., *Chlamydophila* spp., *Cladosporium* spp., *Clostridium* spp., *Clostridiisalibacter* spp., *Cohnella* spp., *Corynebacterium* spp., *Coxiella* spp., *Cronobacter* spp., *Cryptococcus* spp., *Dendrosporobacter* spp., *Desulfotomaculum* spp., *Desulfosporomusa* spp., *Desulfosporosinus* spp., *Desulfovibrio* spp., *Desulfovirgula* spp., *Desulfunispora* spp., *Desulfurispora* spp., *Ehrlichia* spp., *Enterobacter* spp., *Enterococcus* spp., *Escherichia* spp., *Ferrobacillus* spp., *Filifactor* spp., *Filobacillus* spp., *Francisella* spp., *Fusarium* spp., *Fusobacterium* spp., *Gallionella* spp., *Gardnerella* spp., *Gelria* spp., *Geobacillus* spp., *Geosporobacter* spp., *Gracilibacillus* spp., *Haemophilus* spp., *Halobacillus* spp., *Halonatronum* spp., *Helicobacter* spp., *Heliobacterium* spp., *Heliophilum* spp., *Hormoconis* spp., *Klebsiella* spp., *Laceyella* spp., *Lactobacillus* spp., *Lactococcus* spp., *Legionella* spp., *Lentibacillus* spp., *Lepiothrix* spp., *Listeria* spp., *Lysinibacillus* spp., *Megasphaera* spp., *Mahella* spp., *Metabacterium* spp., *Methanobacterium* spp., *Microbacterium* spp., *Micrococcus* spp., *Moorella* spp., *Moraxella* spp., *Mycobacterium* spp., *Mycoplasma* spp., *Natroniella* spp., *Neisseria* spp., *Oceanobacillus* spp., *Orenia* spp., *Ornithinibacillus* spp., *Oxalophagus* spp., *Oxobacter* spp., *Paenibacillus* spp., *Paraliobacillus* spp., *Pasteurella* spp., *Pediococcus* spp., *Pelospora* spp., *Pelotomaculum* spp., *Penicillium* spp., *Peptostreptococcus* spp., *Piscibacillus* spp., *Planifilum* spp., *Pluralibacter* spp., *Pneumocystis* spp., *Pontibacillus* spp., *Porphyromonas* spp., *Prevotella* spp., *Propionibacterium* spp., *Propionispora* spp., *Proteus* spp., *Pseudomonas* spp., *Ralstonia* spp., *Rhizobium* spp., *Rhodococcus* spp., *Rickettsia* spp., *Rochalimaea* spp., *Rothia* spp., *Saccharomyces* spp., *Salinibacillus* spp., *Salmonella* spp., *Salsuginibacillus* spp., *Seinonella* spp., *Serratia* spp., *Shewanella* spp., *Shigella* spp., *Shimazuella* spp., *Sinorhizobium* spp., *Spirillum* spp., *Sporacetigenium* spp., *Sporoanaerobacter* spp., *Sporobacter* spp., *Sporobacterium* spp., *Sporohalobacter* spp., *Sporolactobacillus* spp., *Sporomusa* spp., *Sporosarcina* spp., *Sporotalea* spp., *Sporotomaculum* spp., *Staphylococcus* spp., *Stenotrophomonas* spp., *Stomatococcus* spp., *Streptococcus* spp., *Syntrophomonas* spp., *Syntrophospora* spp., *Tenuibacillus* spp., *Tepidibacter* spp., *Terribacillus* spp., *Treponema* spp., *Thalassobacillus* spp., *Thermoacetogenium* spp., *Thermoactinomyces* spp., *Thermoalkalibacillus* spp., *Thermoanaerobacter* spp., *Thermoanaeromonas* spp., *Thermobacillus* spp., *Thermoflavimicrobium* spp., *Thermovenabulum* spp., *Thiobacillus* spp., *Thiothrix* spp., *Trichophyton* spp., *Trichosporon* spp., *Tuberibacillus* spp., *Vibrio* spp., *Virgibacillus* spp., *Viridans* spp., *Vulcanobacillus* spp., *Wolbachia* spp., and *Yersinia* spp. In some embodiments, the viable microbial material is a microbe selected from the group of: *Acetobacter aurantius, Acidithiobacillus thiooxidans, Acinetobacter baumannii, Actinomyces israelii, Agrobacterium radiobacter, Agrobacterium tumefaciens, Anaplasma phagocytophilum, Arthrobacter chlorophenolicus, Arthrobacter crystallopoietes, Arthrobacter luteus, Aspergillus brasiliensis, Aspergillus fumigatus, Aspergillus niger, Aureobasidium pullulans, Azorhizobium caulinodans, Azotobacter vinelandii, Bacillus anthracis, Bacillus atrophaeus, Bacillus brevis, Bacillus cereus, Bacillus fusiformis, Bacillus licheniformis, Bacillus megaterium, Bacillus mycoides, Bacillus stearothermophilus, Bacillus subtilis, Bacillus thuringiensis, Bacteroides fragilis, Bacteroides gingivalis, Bartonella henselae, Bartonella quintana, Beggiatoa alba, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Candida albicans, Candida auris, Candida dubliniensis, Candida krusei, Candida glabrata, Candida lusitaniae, Candida parapsilosis, Candida tropicalis, Chlamydia trachomatis, Chlamydophila pneumoniae, Chlamydophila psittaci, Cladosporium cladosporioides, Cladosporium resinae, Clostridium botulinum, Clostridium difficile, Clostridium perfringens, Clostridium sporogenes, Clostridium tetani, Corynebacterium ammoniagenes, Corynebacterium diphtheriae, Corynebacterium fusiforme, Corynebacterium glutamicum, Corynebacterium stationis, Coxiella burnetii, Cronobacter sakazakii, Cryptococcus neoformans, Desulfovibrio africanus, Desulfovibrio desulfuricans, Desulfovibrio salixigens, Desulfovibrio vulgaris, Desulfotomaculum orientis, Desulfotomaculum nigrificans, Ehrlichia chaffeensis, Enterobacter aerogenes, Enterobacter cloacae, Enterococcus avium, Enterococcus durans, Enterococcus faecalis, Enterococcus faecium, Enterococcus galllinarum, Enterococcus hirae, Enterococcus maloratus, Escherichia coli, Ferrobacillus ferrooxidans, Francisella tularensis, Fusobacterium nucleatum, Gallionella ferruginea, Gardnerella vaginalis, Geobacillus stearothermophilus, Haemophilus ducreyi, Haemophilus influenzae, Haemophilus parainfluenzae, Haemophilus pertussis, Haemophilus vaginalis, Helicobacter pylori, Hormoconis resinae, Klebsiella oxytoca, Klebsiella pneumoniae, Lactobacillus acidophilus, Lactobacillus bulgaricus, Lactobacillus casei, Lactobacillus plantarum, Lactococcus lactis, Legionella pneumophila, Leptothrix ochracea, Leptothrix discophora, Leptothrix cholodnii, Leptothrix lopholea, Leptothrix mobilis, Listeria monocytogenes, Methanobacterium extroquens, Microbacterium multiforme, Micrococcus luteus, Moraxella catarrhalis, Moraxella osloensis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium terrae, Mycobacterium tuberculosis, Mycoplasma fermentans, Mycoplasma genitalium, Mycoplasma hominis, Mycoplasma penetrans, Mycoplasma pneumoniae, Mycoplasma mexican, Neisseria gonorrhoeae, Neisseria meningitidis, Paenibacillus glucanolyticus, Pasteurella multocida, Pasteurella tularensis, Penicillium chrysogenum, Pluralibacter gergoviae, Pneumocystis carinii, Pneumocystis murina, Porphyromonas gingivalis, Prevotella melaninogenica, Proteus mirabilis, Proteus vulgaris, Pseudomonas aeruginosa, Pseudomonas fluorescens,*

*Pseudomonas putida, Ralstonia pickettii, Rhizobium leguminosarum, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella bongori, Salmonella carrau, Salmonella concord, Salmonella enterica, Salmonella enteritidis, Salmonella infantis, Salmonella newport, Salmonella schwarzengrund, Salmonella typhi, Salmonella typhimurium, Serratia marcescens, Shewanella oneidensis, Shewanella putrefaciens, Shigella dysenteriae, Shigella flexneri, Shigella sonnei, Sinorhizobium meliloti, Spirillum volutans, Staphylococcus aureus, Staphylococcus epidermidis, Staphylococcus hominis, Stenotrophomonas maltophilia, Stomatococcus mucilaginous, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus gordonii, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Thiobacillus concretivorus, Thiobacillus thioparus, Treponema pallidum, Treponema denticola, Trichophyton interdigitale, Trichophyton mentagrophytes, Trichosporon asahii, Vibrio cholerae, Vibrio comma, Vibrio parahaemolyticus, Vibrio vulnificus, Viridans streptococci, Yersinia enterocolitica, Yersinia pestis*, and *Yersinia pseudotuberculosis*, including drug-resistant strains thereof. In some embodiments, the viable microbial material is a microbe selected from the group of: *Acinetobacter baumannii* (ATCC® 19606™), *Aspergillus brasiliensis* (ATCC® 16404™), *Aspergillus niger* (ATCC® 6275™), *Aspergillus niger* (ATCC® 16404™), *Bordetella pertussis* (ATCC® 12743™), *Campylobacter jejuni* (ATCC® 33291™), *Campylobacter jejuni* (ATCC® 29428™), *Candida albicans* (ATCC® 10231™), *Clostridium difficile* (ATCC® 43598™) *Cronobacter* sakazakii (ATCC® 12868™), *Enterobacter aerogenes* (ATCC® 13048™) *Enterococcus faecalis* (ATCC® 29212™), *Escherichia coli* (ATCC® 10536™) *Escherichia coli* (ATCC® 11229™), *Escherichia coli* 0157:H7 (ATCC® 35150™) *Haemophilus influenzae* (ATCC® 10211™), *Klebsiella oxytoca* (ATCC® 13182™) *Klebsiella pneumoniae* (ATCC® 4352™), *Legionella pneumophila* (ATCC® 33153™) *Listeria monocytogenes* (ATCC® 19117™), *Listeria monocytogenes* (ATCC® 19111™) *Listeria monocytogenes* (ATCC® 7644™), Methicillin Resistant *Staphylococcus aureus* (ATCC® BAA-1683™), Methicillin Resistant *Staphylococcus aureus* (ATCC® 33592™) Multi-drug Resistant *Enterococcus faecium* (ATCC® 51559™), Multi-drug resistant *Klebsiella pneumoniae* (ATCC® 51503™), *Mycobacterium bovis* (ATCC® 35743™) *Mycobacterium terrae* (ATCC® 15755™), *Proteus mirabilis* (ATCC® 9240™) *Pseudomonas aeruginosa* (ATCC® 15442™), *Salmonella enterica* (ATCC® 10708™) *Salmonella enterica* (ATCC® 6539™), *Serratia marcescens* (ATCC® 14756™), *Shigella dysenteriae* (ATCC® 11835™), *Shigella flexneri* (ATCC® 29508™), *Shigella sonnei* (ATCC® 11060™), *Staphylococcus aureus* (ATCC® 6538™), *Staphylococcus epidermidis* (ATCC® 12228™), *Streptococcus pneumoniae* (ATCC® 6305™) *Streptococcus pyogenes* (ATCC® 12384™), *Streptococcus pyogenes* (ATCC® 19615™) *Trichophyton interdigitale* (ATCC® 9533™), *Trichophyton mentagrophytes* (ATCC® 9533™), Vancomycin Resistant *Enterococcus faecalis* (ATCC® 51575™), *Vibrio cholera* (ATCC® 11623™), and *Yersinia enterocolitica* (ATCC® 23715™).

In some embodiments, the viable microbial material is an enveloped virus or a non-enveloped virus. In some embodiments, the viable microbial material is a double-stranded virus or a single-stranded virus. In some embodiments, the viable microbial material is a virus belonging to the family of adenoviridae, asfarviridae, circoviridae, hepadnaviridae, herpesviridae, iridoviridae, papillomavirus, papovaviridae, parvoviridae, poxviridae, arenaviridae, arteriviridae, astroviridae, birnaviridae, bunyaviridae, caliciviridae, coronaviridae, filoviridae, flaviviridae, nodaviridae, orthomyxoviridae, paramyxoviridae, picornaviridae, reoviridae, retroviridae, rhabdoviridae, togaviridae, or pneumoviridae. In some embodiments, the virus belongs to a genus selected from the group of: an ebolavirus, an influenza virus, a parainfluenza virus, an enterovirus (e.g., a rhinovirus), an orthopneumovirus, a metapneumovirus, a lentivirus, and a papillomavirus. In some embodiments, the virus is the Duck Hepatitis B virus, the Bovine Viral Diarrhea virus, or the Feline Calicivirus.

Additional non-limiting examples of microbes and viruses that can be included in any of the methods or articles are provided herein. Additional microbes and viruses that can be included in any of the methods or articles described herein are known in the art.

In some embodiments of any of the compositions or methods described herein, the viable microbial material can be naturally occurring or genetically modified. Non-limiting examples of the sources of viable microbial material in any of methods or articles provided herein include a laboratory collection and an environmental sample. In some embodiments, the viable microbial material is sourced from a preserved collection of reference microorganisms (e.g., the ATCC® Bacteriology Collection). In some embodiments, the viable microbial material is isolated from an environmental sample (e.g., a clinical sample collected from a human subject (e.g., a wound of a human subject) or isolated from an environmental sample collected from a surface (e.g., a surface of an object in a hospital or a surface of an object in a manufacturing plant)). Other methods of collecting and isolating viable microbial material may be utilized.

In some embodiments of any of the methods or articles described herein, the viable microbial material comprises between 3.0 logs to 9.5 logs (e.g., between 3.0 logs to 9.0 logs, between 3.0 logs to 8.5 logs, between 3.0 logs to 8.0 logs, between 3.0 logs to 7.5 logs, between 3.0 logs to 7.0 logs, between 3.0 logs to 6.5 logs, between 3.0 logs to 6.0 logs, between 3.0 logs to 5.5 logs, between 3.0 logs to 5.0 logs, between 3.0 logs to 4.5 logs, between 3.0 logs to 4.0 logs, between 3.0 logs to 3.5 logs, between 3.5 logs to 9.5 logs between 3.5 logs to 9.0 logs, between 3.5 logs to 8.5 logs, between 3.5 logs to 8.0 logs, between 3.5 logs to 7.5 logs, between 3.5 logs to 7.0 logs, between 3.5 logs to 6.5 logs, between 3.5 logs to 6.0 logs, between 3.5 logs to 5.5 logs, between 3.5 logs to 5.0 logs, between 3.5 logs to 4.5 logs, between 3.5 logs to 4.0 logs, between 4.0 logs to 9.5 logs, between 4.0 logs to 9.0 logs, between 4.0 logs to 8.5 logs, between 4.0 logs to 8.0 logs, between 4.0 logs to 7.5 logs, between 4.0 logs to 7.0 logs, between 4.0 logs to 6.5 logs, between 4.0 logs to 6.0 logs, between 4.0 logs to 5.5 logs, between 4.0 logs to 5.0 logs, between 4.0 logs to 4.5 logs, between 4.5 logs to 9.5 logs, between 4.5 logs to 9.0 logs, between 4.5 logs to 8.5 logs, between 4.5 logs to 8.0 logs, between 4.5 logs to 7.5 logs, between 4.5 logs to 7.0 logs, between 4.5 logs to 6.5 logs, between 4.5 logs to 6.0 logs, between 4.5 logs to 5.5 logs, between 4.5 logs to 5.0 logs, between 5.0 logs to 9.5 logs, between 5.0 logs to 9.0 logs, between 5.0 logs to 8.5 logs, between 5.0 logs to 8.0 logs, between 5.0 logs to 7.5 logs, between 5.0 logs to 7.0 logs, between 5.0 logs to 6.5 logs, between 5.0 logs to 6.0 logs, between 5.0 logs to 5.5 logs, between 5.5 logs to 9.5 logs, between 5.5 logs to 9.0 logs, between 5.5 logs to 8.5 logs, between 5.5 logs to 8.0 logs, between 5.5 logs to 7.5 logs, between 5.5 logs to 7.0 logs, between 5.5 logs to 6.5 logs, between 5.5 logs to 6.0 logs, between 6.0 logs to 9.5 logs, between 6.0 logs to 9.0 logs, between 6.0 logs to 8.5 logs, between 6.0 logs to 8.0 logs, between 6.0 logs to 7.5 logs, between 6.0 logs to 7.0 logs, between 6.0 logs to 6.5 logs, between 6.5 logs to 9.5 logs, between 6.5 logs to 9.0 logs, between 6.5 logs to 8.5 logs, between 6.5 logs to 8.0 logs, between 6.5 logs to 7.5 logs, between 6.5 logs to 7.0 logs, between 7.0 logs to 9.5 logs, between 7.0 logs to 9.0 logs, between 7.0 logs to 8.5 logs, between 7.0 logs to 8.0 logs, between 7.0 logs to 7.5 logs, between 7.5 logs to 9.5 logs, between 7.5 logs to 9.0 logs, between 7.5 logs to 8.5 logs, between 7.5 logs to 8.0 logs, between 8.0 logs to 9.5 logs, between 8.0 logs to 9.0 logs, between 8.0 logs to 8.5 logs, between 8.5 logs to 9.5 logs, or between 8.5 logs to 9.0 logs) of viable microbial material.

Methods for quantifying the amount of viable microbial material are known in the art.

Substrates

Non-limiting examples of non-water soluble substrates that can be included in any of the test articles are described below.

In some examples, the substrate is a disc, a rectangle, a sphere, a rod, a cylinder, a test tube, or a peg. In some examples, the substrate is a penicylinder (e.g., a flat face penicylinder or a beveled edge penicylinder). In some examples, the substrate the surface of a container or reservoir. In some examples, a porous or non-porous substrate may be desirable in order to replicate a real world application, e.g., various uses of disinfectants. Other substrates for any of the articles describe herein are contemplated. As can be appreciated by those skilled in the art, a specific substrate may be desirable for an organism or for an application.

In any of the test articles described herein, the substrate can have various dimensions depending on its shape and features. Non-limiting examples of substrate material, shape, dimensions, and other features are described below.

In some examples, the substrate comprises metal, metal alloy, glass, plastic, rubber (e.g., a natural rubber or a synthetic rubber), carpet, textile, or wood. In some examples, the substrate comprises stainless steel (e.g., 304 grade, 306 grade, 316 L grade, 316 grade, or 416 grade stainless steel), titanium, titanium alloy, polypropylene, silica, silicone, Teflon®, polycarbonate, acrylonitrile butadiene styrene, aluminum, anodized aluminum alloy, brass, nitrile rubber, silicone rubber, chlorosulfonated polyethylene synthetic rubber, cast iron, cobalt-chrome, granite, marble, quartz, Terrazzo tile, vinyl polymer, polyvinyl chloride, chlorinated polyvinyl chloride, epoxy, carbon steel, copper, ductile iron, ethylene propylene diene monomer rubber, borosilicate glass, ceramic (e.g., porcelain), hydroxyapatite, Lucitone™, nickel, nylon, polyether ether ketone, polystyrene, polytetrafluoroethylene, polyurethane, Viton®, polyethylene (e.g., polyethylene terephthalate glycol, polyethylene terephthalate, low density polyethylene, high density polyethylene, or ultra-high-molecular-weight polyethylene), methyl methacrylate, cement, sand, grout, paint, sealant, fiberglass, polyester, Lexan®, Plexiglas®, Kydex®, acrylic, or Aclar®. In other examples, the substrate comprises dextran, cellulose, or collagen. In other examples, the substrate comprises a polysaccharide or a disaccharide (e.g., glycosaminoglycan). In some embodiments, the substrate is a flexible material, e.g., a material with the ability to bend or compress without cracking. In some examples, the substrate is a rigid or non-flexible material, e.g., a material that is not bendable. Flexible and rigid, non-flexible materials may be utilized.

In some examples, the substrate is a disc (e.g., a borosilicate glass disc, a stainless steel disc, or a disc comprising any of the exemplary materials provided herein). In some examples, the disc substrate can have a diameter of between about 5 mm and about 50 mm (e.g., between about 5 mm and about 45 mm, between about 5 mm and about 40 mm, between about 5 mm and about 35 mm, between about 5 mm and about 30 mm, between about 5 mm and about 25 mm, between about 5 mm and about 20 mm, between about 5 mm and about 15 mm, between about 5 mm and about 10 mm, between about 9 mm and about 15 mm, between about 9 mm and about 13 mm, between about 9 mm and about 11 mm, between about 10 mm and about 50 mm, between about 10 mm and about 40 mm, between about 10 mm and about 30 mm, between about 10 mm and about 20 mm, between about 10 mm and about 15 mm, between about 12 mm and about 15 mm, between about 12 mm and about 14 mm, between about 12 mm and about 13 mm, between about 20 mm and about 50 mm, between about 20 mm and about 40 mm, between about 20 mm and about 30 mm, between about 20 mm and about 25 mm, between about 30 mm and about 50 mm, between about 30 mm and about 40 mm, between about 30 mm and about 35 mm, between about 40 mm and about 50 mm, between about 40 mm and about 45 mm, or between about 45 mm and about 50 mm). In some examples, the disc substrate can have a thickness of between about 0.1 mm and about 10 mm (e.g., between about 0.1 mm and about 9 mm, between about 0.1 mm and about 8 mm, between about 0.1 mm and about 7 mm, between about 0.1 mm and about 6 mm, between about 0.1 mm and about 5 mm, between about 0.1 mm and about 4 mm, between about 0.1 mm and about 3 mm, between about 0.1 mm and about 2 mm, between about 0.1 mm and about 1 mm, between about 0.5 mm and about 1.5 mm, between about 0.5 mm and about 1.25 mm, between about 0.5 mm and about 1 mm, between about 0.5 mm and about 0.75 mm, between about 0.75 mm and about 1 mm, between about 0.75 mm and about 0.95 mm, between about 0.75 mm and about 0.9 mm, between about 0.75 mm and about 0.85 mm, between about 1 mm and about 2 mm, between about 2 mm and about 3 mm, between about 3 mm and about 4 mm, between about 3.5 mm and about 4 mm, between about 3.75 mm and about 3.85 mm, between about 4 mm and about 5 mm, between about 5 mm and about 6 mm, between about 6 mm and about 7 mm, between about 7 mm and about 8 mm, between about 8 mm and about 9 mm, or between about 9 mm and about 10 mm). In some embodiments of the articles described herein, the substrate is a borosilicate glass disc with a diameter of between about 12.5 mm and about 12.9 mm, and a thickness of between about 3.6 mm to about 4.0 mm. In other embodiments, the substrate is a stainless steel disc with a diameter of between about 9.8 mm and about 10.2 mm, and a thickness of between about 0.6 mm to about 1 mm.

In some examples, the substrate is a glass rectangle (e.g., a borosilicate glass cover slip or a borosilicate glass slide). In some examples, the substrate is a carpet rectangle, a stainless steel rectangle, a ceramic rectangle, or a wood rectangle. In some examples, the rectangle substrate can have a length and/or width of between about 2.5 mm and about 500 mm (e.g., between about 5 mm and about 400 mm, between about 5 mm and about 300 mm, between about 5 mm and about 200 mm, between about 5 mm and about 100 mm, between about 5 mm and about 50 mm, between about 5 mm and about 25 mm, between about 5 mm and about 15 mm, between about 10 mm and about 100 mm, between about 50 mm and about 300 mm, between about 50 mm and about 200 mm, between about 50 mm and about 150 mm, between about 100 mm and about 500 mm, between about 100 mm and about 250 mm, between about 100 mm and about 150 mm, between about 200 mm and about 500 mm, between about 200 mm and about 400 mm, between about 200 mm and about 300 mm, between about 300 mm and about 500 mm, between about 300 mm and about 400 mm, between about 400 mm and about 500 mm, between about 20 mm and about 100 mm, between about 20 mm and about 90 mm, between about 20 mm and about 80 mm, between about 20 mm and about 70 mm, between about between about 20 mm and about 60 mm, between about 20 mm and about 50 mm, between about 20 mm and about 40 mm, between about 20 mm and about 30 mm, between about 30 mm and about 100 mm, between about 30 mm and about 90 mm, between about 30 mm and about 80 mm, between about 30 mm and about 70 mm, between about 30 mm and about 60 mm, between about 30 mm and about 50 mm, between about 30 mm and about 40 mm, between about 40 mm and about 100 mm, between about 40 mm and about 90 mm, between about 40 mm and about 80 mm, between about 40 mm and about 70 mm, between about 40 mm and about 60 mm, between about 40 mm and about 50 mm, between about 50 mm and about 100 mm, between about 50 mm and about 90 mm, between about 50 mm and about 80 mm, between about 50 mm and about 70 mm, between about 50 mm and about 60 mm, between about 60 mm and about 100 mm, between about 60 mm and about 90 mm, between about 60 mm and about 80 mm, between about 60 mm and about 70 mm, between about 70 mm and about 100 mm, between about 70 mm and about 90 mm, between about 70 mm and about 80 mm, between about 80 mm and about 100 mm, between about 80 mm and about 90 mm, or between about 90 mm and about 100 mm). In some examples, the rectangle substrate can have a thickness of between about 0.05 mm and about 10 mm (e.g., between about 0.05 mm and about 0.15 mm, between about 0.05 mm and about 0.1 mm, between about 0.08 mm and about 0.13 mm, between about 0.1 mm and about 0.2 mm, between about 0.13 mm and about 0.17 mm, between about 0.16 mm and about 0.19 mm, between about 0.19 mm and about 0.25 mm, between about 0.25 mm and about 2 mm, between about 0.25 mm and about 1.75 mm, between about 0.25 mm and about 1.5 mm, between about 0.25 mm and about 1.25 mm, between about 0.25 mm and about 1 mm, between about 0.25 mm and about 0.75 mm, between about 0.25 mm and about 0.5 mm, between about 0.25 mm and about 0.35 mm, between about 0.35 mm and about 0.45 mm, between about 0.45 mm and about 0.55 mm, between about 0.5 mm and about 0.75 mm, between about 0.75 mm and about 1.5 mm, between about 0.75 mm and about 1.25 mm, between about 0.75 mm and about 1 mm, between about 0.8 mm and about 1.2 mm, between about 0.8 mm and about 1 mm, between about 0.9 mm and about 1.1 mm, between about 1 mm and about 1.5 mm, between about 1 mm and about 1.25 mm, between about 1.1 mm and about 1.3 mm, between about 1.5 mm and about 3 mm, between about 2 mm and about 3 mm, between about 3 mm and about 4 mm, between about 4 mm and about 5 mm, between about 5 mm and about 6 mm, between about 6 mm and about 7 mm, between about 7 mm and about 8 mm, between about 8 mm and about 9 mm, or between about 9 mm and about 10 mm). In some embodiments of the articles described herein, the substrate is a glass rectangle with a width of between about 23 mm and about 27 mm, a length of between about 73 mm and about 77 mm, and a thickness of between about 1.0 mm to about 1.2 mm. In other embodiments, the substrate is a glass rectangle with a width of between about 23 mm and about 27 mm, a length of between about 23 mm and about 27 mm, and a thickness of between about 0.4 mm to about 0.7 mm. In some embodiments of the articles described herein, the substrate is a glass rectangle with a width of between about 45 mm and about 55 mm, a length of between about 45 mm and about 55 mm, and a thickness of between about 1.0 mm to about 1.2 mm. In other embodiments, the substrate is a glass rectangle with a width of between about 45 mm and about 55 mm, a length of between about 45 mm and about 55 mm, and a thickness of between about 0.4 mm to about 0.7 mm.

In some examples, the substrate is a stainless steel (e.g., Type 304 stainless steel comprising at least 18% chromium and 8% nickel) penicylinder. In other examples, the substrate is a porcelain penicylinder. In some examples, the penicylinder has an outer diameter between about 5 mm and about 15 mm (e.g., between about 5 mm and about 13 mm, between about 5 mm and about 11 mm, between about 5 mm and about 9 mm, between about 5 mm and about 7 mm, between about 5 mm and about 6 mm, between about 6 mm and about 12 mm, between about 6 mm and about 10 mm, between about 6 mm and about 8 mm, between about 7 mm and about 15 mm, between about 7 mm and about 13 mm, between about 7 mm and about 11 mm, between about 7 mm and about 9 mm, between about 8 mm and about 12 mm, between about 8 mm and about 10 mm, between about 9 mm and about 15 mm, between about 9 mm and about 13 mm, between about 9 mm and about 11 mm, between about 10 mm and about 15 mm, between about 10 mm and about 12 mm, between about 12 mm and about 15 mm, or between about 13 mm and about 15 mm). In some examples, the penicylinder has an inner diameter between about 3 mm and about 13 mm (e.g., between about 3 mm and about 11 mm, between about 3 mm and about 9 mm, between about 3 mm and about 7 mm, between about 3 mm and about 5 mm, between about 4 mm and about 9 mm, between about 4 mm and about 7 mm, between about 4 mm and about 5 mm, between about 5 mm and about 9 mm, between about 5 mm and about 7 mm, between about 6 mm and about 9 mm, between about 6 mm and about 8 mm, between about 7 mm and about 9 mm, between about 8 mm and about 10 mm, between about 9 mm and about 11 mm, between about 10 mm and about 12 mm, or between about 11 mm and about 13 mm). In some examples, the penicylinder has a length between about 5 mm and about 15 mm (e.g., between about 5 mm and about 13 mm, between about 5 mm and about 11 mm, between about 5 mm and about 9 mm, between about 5 mm and about 7 mm, between about 5 mm and about 6 mm, between about 6 mm and about 12 mm, between about 6 mm and about 10 mm, between about 6 mm and about 8 mm, between about 7 mm and about 15 mm, between about 7 mm and about 13 mm, between about 7 mm and about 11 mm, between about 7 mm and about 9 mm, between about 8 mm and about 12 mm, between about 8 mm and about 10 mm, between about 9 mm and about 15 mm, between about 9 mm and about 13 mm, between about 9 mm and about 11 mm, between about 10 mm and about 15 mm, between about 10 mm and about 12 mm, between about 12 mm and about 15 mm, or between about 13 mm and about 15 mm). In some embodiments of the articles described herein, the substrate is a stainless steel penicylinder with an outer diameter of between about 7 mm and about 9 mm, an inner diameter of between about 5 mm and about 7 mm, and a length of between about 9 mm to about 11 mm. In other embodiments, the substrate is a porcelain penicylinder with an outer diameter of between about 7 mm and about 9 mm, an inner diameter of between about 5 mm and about 7 mm, and a length of between about 9 mm to about 11 mm.

In some embodiments of any of the methods or articles described herein, the substrate has a surface area between 10 $mm^2$ to 10,000 $mm^2$ (e.g., between 10 $mm^2$ to 9,000 $mm^2$, between 10 $mm^2$ to 8,000 $mm^2$, between 10 $mm^2$ to 7,000 $mm^2$, between 10 $mm^2$ to 6,000 $mm^2$, between 10 $mm^2$ to 5,000 $mm^2$, between 10 $mm^2$ to 4,000 $mm^2$, between 10 $mm^2$ to 3,000 $mm^2$, between 10 $mm^2$ to 2,000 $mm^2$, between 10 $mm^2$ to 1,000 $mm^2$, between 10 $mm^2$ to 500 $mm^2$, between 10 $mm^2$ to 100 $mm^2$, between 10 $mm^2$ to 50 $mm^2$, between 1,000 $mm^2$ to 10,000 $mm^2$, between 1,000 $mm^2$ to 9,000 $mm^2$, between 1,000 $mm^2$ to 8,000 $mm^2$, between 1,000 $mm^2$ to 7,000 $mm^2$, between 1,000 $mm^2$ to 6,000 $mm^2$, between 1,000 $mm^2$ to 5,000 $mm^2$, between 1,000 $mm^2$ to 4,000 $mm^2$, between 1,000 $mm^2$ to 3,000 $mm^2$, between 1,000 $mm^2$ to 2,000 $mm^2$, 1,000 $mm^2$ to 1,500 $mm^2$, between 1,500 $mm^2$ to 3,000 $mm^2$, between 1,500 $mm^2$ to 2,500 $mm^2$, between 1,500 $mm^2$ to 2,000 $mm^2$, between 2,000 $mm^2$ to 10,000 $mm^2$, between 2,000 $mm^2$ to 9,000 $mm^2$, between 2,000 $mm^2$ to 8,000 $mm^2$, between 2,000 $mm^2$ to 7,000 $mm^2$, between 2,000 $mm^2$ to 6,000 $mm^2$, between 2,000 $mm^2$ to 5,000 $mm^2$, between 2,000 $mm^2$ to 4,000 $mm^2$, between 2,000 $mm^2$ to 3,000 $mm^2$, between 2,000 $mm^2$ to 2,500 $mm^2$, between 2,500 $mm^2$ to 4,000 $mm^2$, between 2,500 $mm^2$ to 3,500 $mm^2$, between 2,500 $mm^2$ to 3,000 $mm^2$, between 3,000 $mm^2$ to 10,000 $mm^2$, between 3,000 $mm^2$ to 9,000 $mm^2$, between 3,000 $mm^2$ to 8,000 $mm^2$, between 3,000 $mm^2$ to 7,000 $mm^2$, between 3,000 $mm^2$ to 6,000 $mm^2$, between 3,000 $mm^2$ to 5,000 $mm^2$, between 3,000 $mm^2$ to 4,000 $mm^2$, between 3,000 $mm^2$ to 3,500 $mm^2$, between 3,500 $mm^2$ to 5,000 $mm^2$, between 3,500 $mm^2$ to 4,500 $mm^2$, between 3,500 $mm^2$ to 4,000 $mm^2$, between 2,500 $mm^2$ to 3,000 $mm^2$, between 4,000 $mm^2$ to 10,000 $mm^2$, between 4,000 $mm^2$ to 9,000 $mm^2$, between 4,000 $mm^2$ to 8,000 $mm^2$, between 4,000 $mm^2$ to 7,000 $mm^2$, between 4,000 $mm^2$ to 6,000 $mm^2$, between 4,000 $mm^2$ to 5,000 $mm^2$, between 4,000 $mm^2$ to 4,500 $mm^2$, between 4,500 $mm^2$ to 6,000 $mm^2$, between 4,500 $mm^2$ to 5,500 $mm^2$, between 4,500 $mm^2$ to 5,000 $mm^2$, between 5,000 $mm^2$ to 6,000 $mm^2$, between 6,000 $mm^2$ to 7,000 $mm^2$, between 7,000 $mm^2$ to 8,000 $mm^2$, between 8,000 $mm^2$ to 9,000 $mm^2$, between 9,000 $mm^2$ to 10,000 $mm^2$, or between 9,500 $mm^2$ to 10,000 $mm^2$).

In some embodiments of any of the methods or articles described herein, the substrate has a flat side with a surface area between 10 $mm^2$ to 10,000 $mm^2$ (e.g., between 10 $mm^2$ to 9,000 $mm^2$, between 10 $mm^2$ to 8,000 $mm^2$, between 10 $mm^2$ to 7,000 $mm^2$, between 10 $mm^2$ to 6,000 $mm^2$, between 10 $mm^2$ to 5,000 $mm^2$, between 10 $mm^2$ to 4,000 $mm^2$, between 10 $mm^2$ to 3,000 $mm^2$, between 10 $mm^2$ to 2,000 $mm^2$, between 10 $mm^2$ to 1,000 $mm^2$, between 10 $mm^2$ to 500 $mm^2$, between 10 $mm^2$ to 100 $mm^2$, between 10 $mm^2$ to 50 $mm^2$, between 1,000 $mm^2$ to 10,000 $mm^2$, between 1,000 $mm^2$ to 9,000 $mm^2$, between 1,000 $mm^2$ to 8,000 $mm^2$, between 1,000 $mm^2$ to 7,000 $mm^2$, between 1,000 $mm^2$ to 6,000 $mm^2$, between 1,000 $mm^2$ to 5,000 $mm^2$, between 1,000 $mm^2$ to 4,000 $mm^2$, between 1,000 $mm^2$ to 3,000 $mm^2$, between 1,000 $mm^2$ to 2,000 $mm^2$, 1,000 $mm^2$ to 1,500 $mm^2$, between 1,500 $mm^2$ to 3,000 $mm^2$, between 1,500 $mm^2$ to 2,500 $mm^2$, between 1,500 $mm^2$ to 2,000 $mm^2$, between 2,000 $mm^2$ to 10,000 $mm^2$, between 2,000 $mm^2$ to 9,000 $mm^2$, between 2,000 $mm^2$ to 8,000 $mm^2$, between 2,000 $mm^2$ to 7,000 $mm^2$, between 2,000 $mm^2$ to 6,000 $mm^2$, between 2,000 $mm^2$ to 5,000 $mm^2$, between 2,000 $mm^2$ to 4,000 $mm^2$, between 2,000 $mm^2$ to 3,000 $mm^2$, between 2,000 $mm^2$ to 2,500 $mm^2$, between 2,500 $mm^2$ to 4,000 $mm^2$, between 2,500 $mm^2$ to 3,500 $mm^2$, between 2,500 $mm^2$ to 3,000 $mm^2$, between 3,000 $mm^2$ to 10,000 $mm^2$, between 3,000 $mm^2$ to 9,000 $mm^2$, between 3,000 $mm^2$ to 8,000 $mm^2$, between 3,000 $mm^2$ to 7,000 $mm^2$, between 3,000 $mm^2$ to 6,000 $mm^2$, between 3,000 $mm^2$ to 5,000 $mm^2$, between 3,000 $mm^2$ to 4,000 $mm^2$, between 3,000 $mm^2$ to 3,500 $mm^2$, between 3,500 $mm^2$ to 5,000 $mm^2$, between 3,500 $mm^2$ to 4,500 $mm^2$, between 3,500 $mm^2$ to 4,000 $mm^2$, between 2,500 $mm^2$ to 3,000 $mm^2$, between 4,000 $mm^2$ to 10,000 $mm^2$, between 4,000 $mm^2$ to 9,000 $mm^2$, between 4,000 $mm^2$ to 8,000 $mm^2$, between 4,000 $mm^2$ to 7,000 $mm^2$, between 4,000 $mm^2$ to 6,000 $mm^2$, between 4,000 $mm^2$ to 5,000 $mm^2$, between 4,000 $mm^2$ to 4,500 $mm^2$, between 4,500 $mm^2$ to 6,000 $mm^2$, between 4,500 $mm^2$ to 5,500 $mm^2$, between 4,500 $mm^2$ to 5,000 $mm^2$, between 5,000 $mm^2$ to 6,000 $mm^2$, between 6,000 $mm^2$ to 7,000 $mm^2$, between 7,000 $mm^2$ to 8,000 $mm^2$, between 8,000 $mm^2$ to 9,000 $mm^2$, between 9,000 $mm^2$ to 10,000 $mm^2$, or between 9,500 $mm^2$ to 10,000 $mm^2$).

Other examples of substrate material, shape, dimensions, and other features are contemplated. As can be appreciated by one skilled in the art, a certain substrate can be selected depending on the specific embodiment and application.

Stabilizing Mixture

Non-limiting examples of stabilizing agents that can be included in the stabilizing mixture in any of the methods or articles provided herein include: a sugar (e.g., a monosaccharide, a disaccharide, a reducing sugar, or a non-reducing sugar), a polyol, a polymer (e.g., an oligosaccharide, a polysaccharide, a cellulose-derivative, or a synthetic polymer), an antioxidant, an amino acid, a surfactant, and a buffer. Surfactants can be present in any of the compositions of the disclosure, e.g., to stabilize and/or enhance the solubility of other constituents. Buffers can be included in any of the compositions of the disclosure, e.g., to stabilize other constituents and/or control pH.

Non-limiting examples of sugars that can be included in any of the compositions provided herein include: glucose, fructose, xylose, arabinose, sorbose, mannose, rhamnose, galactose, trehalose, maltose, lactose, sucrose, melibiose, maltulose, iso-maltulose, and lactulose.

Non-limiting examples of polymers that can be included in any of the compositions provided herein include: raffinose, stachyose, melezitose, mannotriose, maltodextrin, dextran, starch, inulin, ficoll, alginate, chitosan, methylcellulose, hydroxypropyl cellulose, hydroxyethyl cellulose, hypromellose, xanthan gum, guar gum, pectin, carrageen, galactomannan, gellan gum, cellulose acetate phthalate, carboxy-methyl-cellulose, a salt of alginic acid (e.g., sodium alginate), hydroxyl propyl methyl cellulose, gum acacia, locust bean gum, hydroxyethyl cellulose, hydroxypropyl methylcellulose, polyvinyl alcohol, polyvinyl pyrrolidone, gelatin (e.g., hydrolyzed gelatin and unhydrolyzed gelatin), and polyglycolic acid.

Non-limiting examples of polyols that can be included in any of the compositions provided herein include: sorbitol, arabitol, xylitol, mannitol, erythritol, threitol, and glycerol.

Non-limiting examples of antioxidants that can be included in any of the compositions provided herein include: ascorbic acid, citric acid, acetic acid, a tocopherol, propyl gallate, tertiary butylhydroquinone, butylated hydroxyanisole, and butylated hydroxytoluene.

Non-limiting examples of amino acids that can be included in any of the compositions provided herein include: glycine betaine, sodium glutamate, cysteine, cystine, histidine, and methionine.

Non-limiting examples of buffers that can be included in any of the compositions provided herein include: a potassium phosphate (e.g., monopotassium phosphate), a sodium phosphate (e.g., monosodium phosphate and disodium phosphate), sodium acetate, sodium citrate, sodium succinate, histidine, imidazole, ammonium bicarbonate, a carbonate, [Tris(hydroxymethyl)methylamino]propanesulfonic acid (TAPS), 2-(Bis(2-hydroxyethyl)amino)acetic acid (Bicine), Tris(hydroxymethyl)aminomethane (Tris), 3-[N-Tris(hydroxymethyl)methylamino]-2-hydroxypropanesulfonic acid (Tricine), 3-[N-Tris(hydroxymethyl)methylamino]-2-hydroxypropanesulfonic acid (TAPSO), 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), 3-(N-morpholino)propanesulfonic acid (MOPS), Piperazine-N,N'-bis(2-ethanesulfonic acid) (PIPES), Dimethylarsenic acid (Cacodylate), 2-(N-morpholino)ethanesulfonic acid (MES), and N-cyclohexyl-2-aminoethanesulfonic acid (CHES).

Non-limiting examples of surfactants that can be included in any of the compositions provided herein include: a polysorbate (e.g., polysorbate 20, polysorbate 40, polysorbate 60, or polysorbate 80), a poloxamer (e.g., PLURONICS™), polyethylene glycol, polypropylene glycol, polyethylene glycol/polypropylene glycol block copolymers, polyethylene glycol alkyl ethers, polypropylene glycol alkyl ethers, and polyethylene glycol/polypropylene glycol ether block copolymers.

Non-limiting examples of other stabilizing agents that can be included in any of the methods or articles provided herein include: milk (e.g., skimmed milk), liquid growth medium, and propylene glycol. Other stabilizing agents that can be included in any of the methods or articles are contemplated.

The stabilizing mixture in any of the methods or articles described herein can comprise between about 0% to about 25% (e.g., between about 0.001% to about 20%, between about 0.5% to about 25%, between about 0.5% to about 20%, between about 0.5% to about 15%, between about 0.5% to about 10%, between about 0.5% to about 5%, between about 1% to about 25%, between about 1% to about 20%, between about 1% to about 15%, between about 1% to about 10%, between about 1% to about 5%, between about 1% to about 4%, between about 2% to about 25%, between about 2% to about 20%, between about 2% to about 15%, between about 2% to about 10%, between about 2% to about 5%, between about 2% to about 4%, between about 3% to about 25%, between about 3% to about 20%, between about 3% to about 15%, between about 3% to about 10%, between about 3% to about 5%, between about 4% to about 25%, between about 4% to about 20%, between about 4% to about 15%, between about 4% to about 10%, between about 4% to about 8%, between about 4% to about 5%, between about 1.5% to about 25%, between about 1.5% to about 20%, between about 1.5% to about 15%, between about 1.5% to about 10%, between about 1.5% to about 5%, between about 2.5% to about 25%, between about 2.5% to about 20%, between about 2.5% to about 15%, between about 2.5% to about 10%, or between about 2.5% to about 5%) of a stabilizing agent (e.g., any of the exemplary stabilizing agents provided herein) by weight of the stabilizing mixture composition (e.g., w/w or w/v). In at least some instances, the stabilizing mixture included in any of the methods or articles provided herein comprises less than about 15% (e.g., less than about 12%, less than about 10%, less than about 9%, less than about 8%, less than about 7%, less than about 6%, less than about 5%, less than about 4.5%, less than about 4%, less than about 3.5%, less than about 3%, less than about 2.5%, less than about 2%, less than about 1.5%, less than about 1%, or less than about 0.5%) of a stabilizing agent (e.g., any of the exemplary stabilizing agents described herein or known in the art) by weight of the composition (e.g., w/w or w/v).

The stabilizing mixture in any of the methods or articles described herein can comprise between about 0.01 mg to about 1,000 mg (e.g., between about 0.01 mg to about 100 mg, between about 0.01 mg to about 12 mg, between about 0.01 mg to about 6 mg, between about 0.01 mg to about 1 mg, between about 0.05 mg to about 1 mg, between about 0.05 mg to about 4.5 mg, between about 0.05 mg to about 11 mg, between about 0.5 mg to about 130 mg, between about 0.5 mg to about 640 mg, between about 0.5 mg to about 200 mg, between about 0.25 mg to about 100 mg, between about 0.25 mg to about 80 mg, between about 0.25 mg to about 60 mg, between about 0.25 mg to about 40 mg, between about 0.25 mg to about 20 mg, between about 0.25 mg to about 10 mg, between about 0.25 mg to about 5 mg, between about 0.25 mg to about 2.5 mg, between about 0.25 mg to about 2 mg, between about 0.25 mg to about 1 mg, between about 0.5 mg to about 10 mg, between about 0.5 mg to about 9 mg, between about 0.5 mg to about 8 mg, between about 0.5 mg to about 6 mg, between about 0.5 mg to about 5 mg, between about 0.5 mg to about 4 mg, between about 0.5 mg to about 3 mg, between about 0.5 mg to about 2 mg, between about 0.5 mg to about 1 mg, between about 0.5 mg to about 0.75 mg, between about 0.75 mg to about 1 mg, between about 1 mg to about 2 mg, between about 1.25 mg to about 1.75 mg, between about 0.25 mg to about 12 mg, between about 0.25 mg to about 8 mg, between about 0.25 mg to about 1.5 mg, between about 0.5 mg to about 60 mg, between about 0.5 mg to about 4.5 mg, between about 0.5 mg to about 11 mg, between about 0.5 mg to about 130 mg, between about 0.5 mg to about 640 mg, between about 0.5 mg to about 200 mg, between about 0.5 mg to about 2 mg, between about 0.5 mg to about 35 mg, between about 10 mg to about 30 mg, between about 10 mg to about 25 mg, between about 10 mg to about 20 mg, between about 10 mg to about 15 mg, between about 10 mg to about 12.5 mg, between about 10 mg to about 80 mg, between about 10 mg to about 70 mg, between about 10 mg to about 60 mg, between about 10 mg to about 50 mg, between about 10 mg to about 40 mg, between about 15 mg to about 25 mg, between about 17.5 mg to about 22.5 mg, between about 20 mg to about 30 mg, between about 20 mg to about 25 mg, between about 25 mg to about 45 mg, between about 25 mg to about 35 mg, between about 25 mg to about 30 mg, between about 30 mg to about 45 mg, between about 30 mg to about 40 mg, between about 30 mg to about 35 mg, between about 35 mg to about 40 mg, between about 45 mg to about 55 mg, between about 50 mg to about 100 mg, between about 50 mg to about 90 mg, between about 50 mg to about 80 mg, between about 50 mg to about 70 mg, between about 50 mg to about 60 mg, between about 50 mg to about 55 mg, between about 150 mg to about 300 mg, between about 150 mg to about 450 mg, between about 150 mg to about 250 mg, between about 150 mg to about 180 mg, between about 225 mg to about 500 mg, between about 225 mg to about 400 mg, between about 225 mg to about 300 mg, between about 600 mg to about 1,000 mg, between about 600 mg to about 900 mg, between about 20 mg to about 25 mg, between about 20 mg to about 40 mg, between about 20 mg to about 28 mg, between about 20 mg to about 37 mg, between about 750 mg to about 775 mg, between about 750 mg to about 825 mg, between about 800 mg to about 915 mg, between about 75 mg to about 105 mg, between about 75 mg to about 99 mg, between about 30 mg to about 60 mg, between about 30 mg to about 50 mg, between about 30 mg to about 40 mg, between about 4 mg to about 16 mg, between about 4 mg to about 12 mg, between about 4 mg to about 8 mg, between about 3 mg to about 9 mg, between about 3 mg to about 6 mg, between about 2 mg to about 6 mg, between about 2 mg to about 5 mg, between about 12 mg to about 15 mg, between about 12 mg to about 14 mg, between about 15 mg to about 20 mg, or between about 15 mg to about 18 mg) of a stabilizing agent (e.g., any of the exemplary stabilizing agents provided herein) per article or per $cm^2$.

Residual Water Content

Any of the methods or articles provided herein can comprise residual moisture content or residual water content (e.g., a measurable amount of water). Residual water content is the amount of water that remains in the thin microbial layer of the preserved antimicrobial test article. Similar to residual water content, residual moisture content includes not only the amount of remaining water but also other volatile substances that remain in the article's thin microbial layer after preservation. The residual water and moisture content have a significant impact on the stability of any of the preserved antimicrobial test articles described herein. The presence of residual water content can provide conditions for some metabolic activity to continue within the thin microbial layer, contributing to degradation following preservation and during storage. It may be desirable to have minimal residual water and moisture content.

In some examples of the methods or articles described herein the thin microbial layer of the preserved antimicrobial test article can comprise between about 0% to about 25% (e.g., between about 0.001% to about 20%, between about 0.5% to about 25%, between about 0.5% to about 20%, between about 0.5% to about 15%, between about 0.5% to about 10%, between about 0.5% to about 5%, between about 1% to about 25%, between about 1% to about 20%, between about 1% to about 15%, between about 1% to about 10%, between about 1% to about 5%, between about 1% to about 4%, between about 2% to about 25%, between about 2% to about 20%, between about 2% to about 15%, between about 2% to about 10%, between about 2% to about 5%, between about 2% to about 4%, between about 3% to about 25%, between about 3% to about 20%, between about 3% to about 15%, between about 3% to about 10%, between about 3% to about 5%, between about 4% to about 25%, between about 4% to about 20%, between about 4% to about 15%, between about 4% to about 10%, between about 4% to about 8%, between about 4% to about 5%, between about 1.5% to about 25%, between about 1.5% to about 20%, between about 1.5% to about 15%, between about 1.5% to about 10%, between about 1.5% to about 5%, between about 2.5% to about 25%, between about 2.5% to about 20%, between about 2.5% to about 15%, between about 2.5% to about 10%, or between about 2.5% to about 5% water) of residual water content or residual moisture content by weight (e.g., w/w). In at least some instances, the residual water content or residual moisture content of the thin microbial layer in any of the methods or articles provided herein is less than about 15% (e.g., less than about 12%, less than about 10%, less than about 9%, less than about 8%, less than about 7%, less than about 6%, less than about 5%, less than about 4.5%, less than about 4%, less than about 3.5%, less than about 3%, less than about 2.5%, less than about 2%, less than about 1.5%, less than about 1%, or less than about 0.5%) by weight (e.g., w/w). In some instances, the residual water content or residual moisture content of the thin microbial layer is less than about 5% by weight (e.g., w/w or w/v).

Any of the methods or articles described herein can comprise between about 0 mg to about 500 mg (e.g., between about 0.25 mg to about 500 mg, between about 0.25 mg to about 400 mg, between about 0.25 mg to about 300 mg, between about 0.25 mg to about 200 mg, between about 0.25 mg to about 100 mg, between about 0.25 mg to about 50 mg, between about 0.25 mg to about 25 mg, between about 5 mg to about 500 mg, between about 5 mg to about 400 mg, between about 5 mg to about 300 mg, between about 5 mg to about 200 mg, between about 5 mg to about 100 mg, between about 5 mg to about 50 mg, between about 5 mg to about 25 mg, between about 15 mg to about 500 mg, between about 15 mg to about 400 mg, between about 15 mg to about 300 mg, between about 15 mg to about 200 mg, between about 15 mg to about 100 mg, between about 15 mg to about 50 mg, between about 15 mg to about 25 mg, between about 50 mg to about 500 mg, between about 50 mg to about 400 mg, between about 50 mg to about 300 mg, between about 50 mg to about 250 mg, between about 50 mg to about 200 mg, between about 50 mg to about 150 mg, between about 50 mg to about 100 mg, between about 100 mg to about 500 mg, between about 100 mg to about 450 mg, between about 100 mg to about 400 mg, between about 100 mg to about 350 mg, between about 100 mg to about 300 mg, between about 100 mg to about 250 mg, between about 100 mg to about 200 mg, between about 100 mg to about 150 mg, between about 150 mg to about 500 mg, between about 150 mg to about 450 mg, between about 150 mg to about 400 mg, between about 150 mg to about 350 mg, between about 150 mg to about 300 mg, between about 150 mg to about 250 mg, between about 150 mg to about 200 mg, between about 200 mg to about 500 mg, between about 200 mg to about 450 mg, between about 200 mg to about 400 mg, between about 200 mg to about 350 mg, between about 200 mg to about 300 mg, between about 200 mg to about 250 mg, between about 250 mg to about 500 mg, between about 250 mg to about 450 mg, between about 250 mg to about 400 mg, between about 250 mg to about 350 mg, between about 250 mg to about 300 mg, between about 300 mg to about 500 mg, between about 300 mg to about 450 mg, between about 300 mg to about 400 mg, between about 300 mg to about 350 mg, between about 350 mg to about 500 mg, between about 350 mg to about 450 mg, between about 350 mg to about 400 mg, between about 400 mg to about 500 mg, or between about 400 mg to about 450 mg) of residual water content or residual moisture content per article or per $cm^2$. In some examples of any of the methods or articles described herein, the thin microbial layer can comprise less than 500 mg (e.g., less than 450 mg, less than 400 mg, less than 350 mg, less than 300 mg, less than 250 mg, less than 200 mg, less than 175 mg, less than 150 mg, less than 125 mg, less than 100 mg, less than 90 mg, less than 80 mg, less than 70 mg, less than 60 mg, less than 50 mg, less than 45 mg, less than 40 mg, less than 35 mg, less than 30 mg, less than 25 mg, less than 20 mg, less than 15 mg, less than 10 mg, less than 9 mg, less than 8 mg, less than 7 mg, less than 6 mg, less than 5 mg, less than 4 mg, less than 3 mg, less than 2 mg, or less than 1 mg) of residual water content or residual moisture content per article or per $cm^2$.

Other methods for determining residual water content may include the Karl Fisher titration method (see, e.g., Krasucka et al., *Acta Pol. Pharm.* 69: 1364-1367, 2012 and Reh et al., *Food Chem.* 86: 457-464, 2004). Other methods for determining residual moisture content may include loss-on-drying or gravimetric methodology (see, e.g., May et al., *Cryobiology* 26: 277-284, 1989), and using near-infrared spectroscopy (see, e.g., Zheng et al., *J. Pharm. Biomed. Anal.* 46: 592-596, 2008).

Any of the methods or articles provided herein can also be characterized by water activity. In some examples of the methods or articles described herein the article can exhibit a water activity of less than about 0.9 Aw (e.g., less than about 0.85 Aw, less than about 0.8 Aw, less than about 0.75 Aw, less than about 0.7 Aw, less than about 0.65 Aw, less than about 0.6 Aw, less than about 0.55 Aw, less than about 0.5 Aw, less than about 0.45 Aw, less than about 0.4 Aw, less than about 0.35 Aw, less than about 0.3 Aw, less than about 0.25 Aw, less than about 0.2 Aw, less than about 0.15 Aw, less than about 0.1 Aw, or less than about 0.05 Aw). Methods for determining the water activity of a composition at a given temperature may include, e.g., using a resistive electrolytic hygrometer, a capacitance hygrometer, or a dew point hygrometer.

Stability

The stability of the viable microbial material in any of the methods or preserved antimicrobial test articles provided herein can be described by a loss of viability over time. The loss of viability of the viable microbial material in any of the articles described herein can be calculated on a logarithmic scale by subtracting the number of units (e.g., the number of log CFU per composition or per $cm^2$) of the viable microbial material (e.g., any of the exemplary viable microbial material described herein) in the thin microbial layer at a point in time (e.g., at about 30 days, at about 60 days, at about 90 days, at about 180 days, at about 365 days, or at about 730 days) from the number of units of the viable material material following preservation (e.g., within 12 hours of finishing the preservation process). The resulting number is the loss of viability of the viable microbial material over a period of time (e.g., over a period of about 30 days, over a period of about 60 days, over a period of about 90 days, over a period of about 180 days, over a period of about 365 days, or over a period of about 730 days). The stability of a viable microbial material in the preserved antimicrobial test articles described herein can be further characterized by the temperature the article is stored at over a particular period of time for which the loss of viability is determined.

The loss of viability of the viable microbial material in any of the articles described herein can be less than about 5.0 log (e.g., less than about 4.9 log, less than about 4.8 log, less than about 4.7 log, less than about 4.6 log, less than about 4.5 log, less than about 4.4 log, less than about 4.3 log, less than about 4.2 log, less than about 4.1 log, less than about 4 log, less than about 3.9 log, less than about 3.8 log, less than about 3.7 log, less than about 3.6 log, less than about 3.5 log, less than about 3.4 log, less than about 3.3 log, less than about 3.2 log, less than about 3.1 log, less than about 3 log, less than about 2.9 log, less than about 2.8 log, less than about 2.7 log, less than about 2.6 log, less than about 2.5 log, less than about 2.4 log, less than about 2.3 log, less than about 2.2 log, less than about 2.1 log, less than about 2 log, less than about 1.9 log, less than about 1.8 log, less than about 1.7 log, less than about 1.6 log, less than about 1.5 log, less than about 1.4 log, less than about 1.3 log, less than about 1.2 log, less than about 1.1 log, less than about 1 log, less than about 0.9 log, less than about 0.8 log, less than about 0.7 log, less than about 0.6 log, less than about 0.5 log, less than about 0.4 log, less than about 0.3 log, less than about 0.2 log, or less than about 0.1 log) per article or per $cm^2$ over a period of at least about 30 days (e.g., at least about 35 days, at least about 60 days, at least about 90 days, at least about 120 days, at least about 150 days, at least about 180 days, at least about 210 days, at least about 240 days, at least about 270 days, at least about 300 days, at least about 365 days, or at least about 730 days) at a temperature between about 2° C. to about 7° C. (e.g., about 2° C., about 3° C., about 4° C., about 5° C., about 6° C., or about 7° C.). In some embodiments, the loss of viability of the microbial material is less than about 3 log per composition or per $cm^2$ over a period of about 180 days at a temperature of about 5° C. In some embodiments, the loss of viability of the microbial material is less than about 1.0 log per composition or per $cm^2$ over a period of about 180 days at a temperature of about 5° C. In some instances, the loss of viability of the microbial material in any of the methods or articles provided herein is less than 0.5 log per article or per $cm^2$ over a period of about 180 days at a temperature of about 5° C.

In some embodiments, the loss of viability of the microbial material in any of the methods or articles described herein can be less than about 5 log (e.g., less than about 4.9 log, less than about 4.8 log, less than about 4.7 log, less than about 4.6 log, less than about 4.5 log, less than about 4.4 log, less than about 4.3 log, less than about 4.2 log, less than about 4.1 log, less than about 4 log, less than about 3.9 log, less than about 3.8 log, less than about 3.7 log, less than about 3.6 log, less than about 3.5 log, less than about 3.4 log, less than about 3.3 log, less than about 3.2 log, less than about 3.1 log, less than about 3 log, less than about 2.9 log, less than about 2.8 log, less than about 2.7 log, less than about 2.6 log, less than about 2.5 log, less than about 2.4 log, less than about 2.3 log, less than about 2.2 log, less than about 2.1 log, less than about 2 log, less than about 1.9 log, less than about 1.8 log, less than about 1.7 log, less than about 1.6 log, less than about 1.5 log, less than about 1.4 log, less than about 1.3 log, less than about 1.2 log, less than about 1.1 log, less than about 1 log, less than about 0.9 log, less than about 0.8 log, less than about 0.7 log, less than about 0.6 log, less than about 0.5 log, less than about 0.4 log, less than about 0.3 log, less than about 0.2 log, or less than about 0.1 log) per article or per $cm^2$ over a period of at least about 30 days (e.g., at least about 35 days, at least about 60 days, at least about 90 days, at least about 120 days, at least about 150 days, at least about 180 days, at least about 210 days, at least about 240 days, at least about 270 days, at least about 300 days, at least about 365 days, or at least about 730 days) at a temperature between about 20° C. to about 25° C. (e.g., about 20° C., about 21° C., about 22° C., about 23° C., about 24° C., or about 25° C.). In some instances, the loss of viability of the microbial material in any of the methods or articles provided herein is less than 1.0 log per article or per $cm^2$ over a period of about 90 days at a temperature between about 20° C. to about 25° C.

Methods for quantifying the amount of viable microbial material are known in the art.

Methods of Manufacturing

Figure 4:
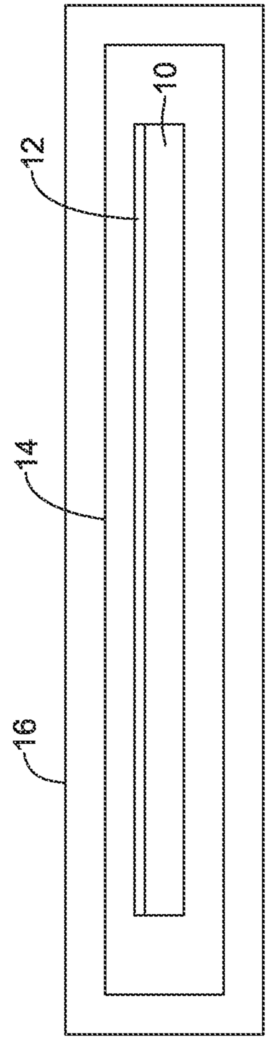
FIG. 4 schematically depicts an example substrate with a layer of microbial material disposed thereon disposed in a primary container and a secondary container.

The present disclosure provides a method to manufacture a preserved antimicrobial test article (e.g., for use in evaluating the antimicrobial efficacy of a hard surface disinfectant or sanitizer). The present disclosure provides a method to manufacture a preserved antimicrobial test article that is surprisingly stable for a significant period of time (e.g., 90 days) and is capable of being used in an antimicrobial assay after having been stored for a significant amount of time (e.g., 90 days, 180 days, or 365 days). The present disclosure provides a method to manufacture a preserved antimicrobial test article that may perform similar to, indicative of, or the same as a freshly-prepared test article, even after having been stored for a significant amount of time. The method comprises suspending a concentrated pellet of viable microbial material (e.g., any of the viable microbial material described herein) in a predetermined amount of a solution comprising a stabilizing mixture (e.g., any of the stabilizing mixtures described herein) to create a suspension with a predetermined amount of viable microbial material per volume and agitating the suspension until the viable microbial material and stabilizing mixture are homogenously dispersed throughout the suspension. The method further comprises depositing a predetermined amount of the suspension onto a non-water soluble substrate to create a thin microbial layer comprising viable microbial material and a stabilizing mixture, and dehydrating the thin microbial layer (e.g., to a residual water content of less than 5%). In some examples, the method further comprises sealing the dehydrated antimicrobial test article in a container. In some examples of the methods provided herein, the article comprises viable microbial material with a loss of viability of less than 0.5 log over at least 30 days at 4° C. In some examples, the article is used in evaluating the antimicrobial efficacy of a hard surface disinfectant or sanitizer (i) directly from the preserved state without rehydration and (ii) without detaching the layer comprising the viable microbial material from the substrate prior to contact with a test sample/substance. In some examples of any of the methods of manufacturing described herein, the article is disposed within a primary container (e.g., a primary container 14 as shown in FIG. 3) and the primary container is sealed within a secondary container (e.g., a secondary container 16 as shown in FIG. 4) that has low permeability to moisture and oxygen. In some examples, the primary container, the secondary container, or both are impermeable to moisture and oxygen. In some examples, a desiccant is disposed within the secondary container. In some examples, an oxygen scavenger is disposed within the secondary container. In some examples, the concentrated pellet is prepared by centrifuging a suspension of viable microbial cells with a concentration between $1.0\times10^4$ and $1\times10^9$ per mL.

In some examples, the stabilizing mixture comprises a sugar. In some examples, the sugar is a non-reducing sugar. In some examples, the stabilizing mixture further comprises an antioxidant. In some examples, the stabilizing mixture comprises a growth nutrient. In some examples, the stabilizing mixture comprises a buffer. In some examples, the stabilizing mixture comprises between 1% and 15% of a sugar, between 1% and 15% of an antioxidant, and one or both of a growth nutrient and a buffer. In some examples, the stabilizing mixture comprises between 5% and 15% of a sugar, between 2% and 10% of an antioxidant, and one or both of a growth nutrient and a buffer. In some examples, the stabilizing mixture further comprises a soil load. In some examples, the soil load is between 1% to 15% by weight. In some examples, the soil load comprises an organic salt. In some examples, the soil load comprises bovine serum. In some examples, the stabilizing mixture comprises a pH of between 6.4 and 8.4. In some examples, the stabilizing mixture comprises a pH of between 6.9 and 7.9. In some examples, the stabilizing mixture comprises a pH of between 7.2 and 7.6. In some examples, the stabilizing mixture comprises a pH of 7.4. In some examples, after resuspension the viable microbial material has a concentration between $1.0\times10^4$ and $1\times10^9$ CFU per mL. In some examples, after resuspension the viable microbial material has been concentrated by a factor of between 2 and 10. In some examples, after resuspension the viable microbial material has been concentrated by a factor of between 4 and 10. In some examples, after resuspension the viable microbial material has been concentrated by a factor of between 4 and 6. In some examples, a volume of between 5 μL and 30 μL of the suspension is deposited onto the non-water soluble substrate to create the thin microbial layer. In some examples, the antimicrobial test article can be dehydrated using a process that comprises freezing and lyophilizing. In some examples of any of the methods provided herein, the antimicrobial test article can be dehydrated using a process that includes air drying. In some examples, the article can be dehydrated using a process that includes an incubator or heated chamber. In some examples, the article can be dehydrated under pressure. In some examples, the article can be dehydrated using a process that includes a desiccator (e.g., a non-vacuum desiccator or a vacuum desiccator).

Method of Evaluating Antimicrobial Efficacy

The present disclosure provides a method to evaluate the antimicrobial efficacy of a test sample (e.g., a test substance or other item that is to be tested for antimicrobial efficacy). The present disclosure also provides a method to evaluate the antimicrobial efficacy of a disinfectant or a sanitizer. The method comprises using any suitable example embodiment of a preserved antimicrobial test article described herein with a test sample/substance suspected of antimicrobial efficacy. In some embodiments, method of evaluating the antimicrobial efficacy of a test sample/substance comprises removing a preserved antimicrobial test article from a sealed container, contacting the preserved antimicrobial test article with a predetermined amount of the test sample/substance without rehydrating the preserved microbial article and without detaching the layer comprising the viable microbial material from the substrate prior to contact with the test sample/substance, maintaining contact between the antimicrobial test article and the test sample/substance for a predetermined test contact time, contacting the antimicrobial test article and the test sample/substance with a neutralizer after the test contact time, agitating the antimicrobial test article, and observing an indication of antimicrobial efficacy. In some examples, the preserved antimicrobial test article comprises a non-water soluble substrate, and a thin microbial layer attached to the substrate comprising viable microbial material and a stabilizing mixture. In some examples, the thin microbial layer of the preserved antimicrobial test article comprises a residual water content of less than 5.0%. In some examples, the viable microbial material has a loss of viability of less than 0.5 logs over at least 30 days at 5° C. In some examples, the article is sealed in a container. In some examples, the article is used in evaluating the antimicrobial efficacy of a hard surface disinfectant or sanitizer (i) directly from the preserved state without rehydration and (ii) without detaching the layer comprising the viable microbial material from the substrate prior to contact with a test sample/substance. In some examples, the preserved antimicrobial test article is incubated at a predetermined temperature for a predetermined amount of time prior to contacting the preserved antimicrobial test article with the test sample/substance.

Kits

Also included herein are kits that include at least one of any of the articles described herein. In some examples, a kit includes multiple (e.g., two, three, four, five, six, seven, eight, nine, ten, twelve, eighteen, twenty-four, thirty, thirty-six, forty-eight, fifty-four, sixty, seventy, eighty, ninety, ninety-six, one-hundred, or more than one-hundred) articles (e.g., any of the articles described herein). In some examples, a kit includes an article comprising a microbial organism and a different article comprising a different microbial organism. In some examples of any of the kits, the article(s) are enclosed within a primary container. In some examples, more than one article is enclosed within a single primary container. In some examples, one or more primary container(s) are then sealed within a secondary container (e.g., a moisture barrier bag or a foil bag) that has low permeability to moisture and oxygen. In some embodiments, the primary container has low permeability to moisture and/or oxygen. In some embodiments, the secondary container further comprises a desiccant (e.g., any of the exemplary desiccants provided here) or an oxygen scavenger (e.g., any of the exemplary oxygen scavengers provided here).

Some examples of any of the kits provided herein further include a buffer, a dye, or a stain. Some examples further include materials and/or consumables (e.g., a 50 mL conical tube) used to conduct an assay (e.g., an assay for measuring antimicrobial activity of a compound). Some examples include a nutrient media to support the growth of microorganisms, e.g., to plate and count colony forming units, e.g., after testing for antimicrobial activity. Some examples of any of the kits provided herein further include an antimicrobial substance (e.g., an antimicrobial drug or a disinfectant), e.g., to be used as a part of a control sample in an assay. Any of the kits provided herein can be used to determine the anti-microbial activity of a test sample/substance, e.g., that is formulated as a solution, a liquid, a towelette, a wipe, a spray, a powder, a gel, or a paste.

In some examples, a kit for evaluating the antimicrobial efficacy of a hard surface disinfectant or sanitizer comprises: a preserved antimicrobial test article comprising: a non-water soluble substrate, a thin microbial layer attached to the substrate comprising viable microbial material, a stabilizing mixture, and a residual water content of less than 5.0%, wherein the thin microbial layer comprises between 3.0 logs to 9.0 logs of viable microbial material, wherein the viable microbial material has a loss of viability of less than 0.5 log over at least 30 days at 4° C., wherein the article is sealed in a container, wherein the article is used in evaluating the antimicrobial efficacy of a hard surface disinfectant or sanitizer (i) directly from the preserved state without rehydration and (ii) without detaching the layer comprising the viable microbial material from the substrate prior to contact with a test sample/substance. In some examples of any of the kits described herein, an article is disposed within a primary container and the primary container is sealed within a secondary container that has low permeability to moisture and oxygen. In some examples, the primary container, the secondary container, or both are impermeable to moisture and oxygen. In some examples, a desiccant is disposed within the secondary container. In some examples, an oxygen scavenger is disposed within the secondary container.

Examples

The disclosure may be further clarified by reference to the following Examples, which serve to exemplify some embodiments, and not to limit the disclosure in any way.

Example 1—Stability of Preserved *S. aureus* Antimicrobial Test Articles with 10% Sucrose/6% Ascorbate Over 3 Months

*Staphylococcus aureus* (ATCC® 6538™) was grown in nutrient broth and in synthetic broth for 48 hours at 35° C. The cells were then concentrated in a stabilizing mixture comprising 10% w/v sucrose, 6% w/v ascorbate, and their respective broth medias. 10 μL of the each of the cell solutions comprising the stabilizing mixture were coated onto sterile 1"×1" glass slides to create test articles. The test articles were then air dried at room temperature (approximately 23° C.) for approximately 40 minutes or until the coated cell solution was substantially evaporated. Each set of test articles were then sealed into a moisture barrier package (aluminum mylar pouch) that also contained 10 g silica desiccant and 500 cc oxygen scavenger. The packaged test articles were then stored at room temperature for 3 months. Additional sets of the 10% sucrose, 6% ascorbate, and synthetic broth test articles were stored at 4° C. and at 36° C. After 3 months, the preserved test articles were then removed from their respective sealed mylar pouch, the cells were recovered from the test articles and the colony forming units (CFUs) were enumerated using serial dilutions and trypticase soy agar (TSA) media. A 1 week data point was also collected for both formulations under 36° C. storage conditions. The inoculated TSA plates were placed into a 35° C. incubator for approximately 18 hours. The colony counts are shown below. Three replicates for each data point were collected. SD=standard deviation.

TABLE 1

Preserved test articles stored at room temperature for 3 months (log 10 CFU/test article)

| Cell Coating Formulation | T = 0 | T = 0 Average (SD) | T = 3 Months | T = 3 Months Average (SD) | Log Loss from T = 0 |
|---|---|---|---|---|---|
| 10% sucrose, 6% ascorbic acid, synthetic broth | 6.35<br>6.35<br>6.51 | 6.40 (0.09) | 6.40<br>6.10<br>6.50 | 6.33 (0.21) | 0.07 |
| 10% sucrose, 6% ascorbic acid, nutrient broth | 6.60<br>6.30<br>6.35 | 6.42 (0.16) | 6.50<br>6.10<br>6.40 | 6.33 (0.21) | 0.09 |

These results show that preserved test articles surprisingly had very little loss of viability after 3 months at room temperature. The log loss of the preserved test articles over 3 months was less than the standard deviation of the log CFU per test article at time zero.

TABLE 2

Preserved test articles stored at various temperatures for 3 months (log 10 CFU/test article)

| Cell Coating Formulation | Storage Temperature | T = 0 Average (SD) | T = 3 months Average (SD) | Log Loss from T = 0 |
|---|---|---|---|---|
| 10% sucrose, 6% ascorbic acid, synthetic broth | 4° C. | 6.40 (0.09) | 6.27 (0.12) | 0.13 |
| | 23° C. | 6.40 (0.09) | 6.33 (0.21) | 0.07 |
| | 36° C. | 6.40 (0.09) | 5.93 (0.31) | 0.47 |

These results show that preserved test articles surprisingly had very little loss of viability after 3 months, even when stored at a highly elevated temperature (36° C.) for the full 3 months.

TABLE 3

| Preserved test articles stored at 36° C. for 1 week (log 10 CFU/test article) | | |
|---|---|---|
| Cell Coating Solution | T = 0 Average (SD) | T = 1 Week Average (SD) |
| 10% sucrose, 6% ascorbic acid, synthetic broth | 6.40 (0.09) | 6.28 (0.24) |
| 10% sucrose, 6% ascorbic acid, nutrient broth | 6.42 (0.16) | 6.57 (0.11) |

These results show that preserved test articles surprisingly had very little loss of viability after 1 week when stored at a highly elevated temperature (36° C.).

Example 2—Stability of Preserved *S. aureus* Antimicrobial Test Articles with 2% Sucrose Over 1 Week

*Staphylococcus aureus* (ATCC® 6538™) was grown in nutrient broth for 48 hours at 35° C. The cells were then concentrated in a stabilizing mixture comprising 2% w/v sucrose and nutrient broth. 10 μL of the cell solution comprising the stabilizing mixture was coated onto sterile 1"×1" glass slides to create test articles. The test articles were then air dried at room temperature (approximately 23° C.) for approximately 40 minutes or until the coated cell solution was substantially evaporated. Each set of test articles were then sealed into a moisture barrier package (aluminum mylar pouch) that also contained 10 g silica desiccant and 500 cc oxygen scavenger. The packaged test articles were then stored at 23° C. and at 46° C. for 1 week. At 1 day, 3 days, and 1 week the preserved test articles were removed from their respective sealed mylar pouch, the cells were recovered from the test articles and the colony forming units (CFUs) were enumerated using serial dilutions and trypticase soy agar (TSA) media. The inoculated TSA plates were placed into a 35° C. incubator for approximately 18 hours. The colony counts are shown below. Three replicates for each data point were collected. SD=standard deviation.

TABLE 4

| Preserved test articles stored at various temperatures for 1 week | | | | | |
|---|---|---|---|---|---|
| Time Point | Storage Temperature | Log 10 CFU/Test Article | Average Log 10 CFU/Test Article | SD | Log Loss from T = 0 |
| T = 0 | N/A | 6.94 | 6.81 | 0.12 | N/A |
| | | 6.80 | | | |
| | | 6.70 | | | |
| T = 1 day | 23° C. | 6.93 | 6.92 | 0.07 | −0.11 |
| | | 6.99 | | | |
| | | 6.85 | | | |
| T = 1 day | 46° C. | 6.74 | 6.74 | 0.08 | 0.08 |
| | | 6.81 | | | |
| | | 6.65 | | | |
| T = 3 days | 23° C. | 6.76 | 6.89 | 0.19 | −0.07 |
| | | 7.11 | | | |
| | | 6.80 | | | |
| T = 3 days | 46° C. | 6.51 | 6.45 | 0.06 | 0.36 |
| | | 6.44 | | | |
| | | 6.40 | | | |

TABLE 4-continued

| Preserved test articles stored at various temperatures for 1 week | | | | | |
|---|---|---|---|---|---|
| Time Point | Storage Temperature | Log 10 CFU/Test Article | Average Log 10 CFU/Test Article | SD | Log Loss from T = 0 |
| T = 7 days | 23° C. | 6.83 | 6.88 | 0.06 | −0.07 |
| | | 6.88 | | | |
| | | 6.94 | | | |
| T = 7 days | 46° C. | 6.44 | 6.29 | 0.25 | 0.52 |
| | | 6.00 | | | |
| | | 6.44 | | | |

These results show that preserved test articles surprisingly had very little loss of viability at room temperature (23° C.) and at an extremely elevated temperature (46° C.) over 1 week.

Example 3—Stability of Preserved *K. pneumoniae* Antimicrobial Test Articles with 2% Sucrose/5% Fetal Bovine Serum (FBS) Over 6 Months

*Klebsiella pneumoniae* (ATCC® 4352™) was grown in nutrient broth for 48 hours at 35° C. The cells were then concentrated in a stabilizing mixture comprising 2% w/v sucrose, 5% FBS, and nutrient broth. 10 μL of the cell solution comprising the stabilizing mixture was coated onto sterile 1"×1" glass slides to create test articles. The test articles were then air dried at room temperature (approximately 23° C.) for approximately 40 minutes or until the coated cell solution was substantially evaporated. Each set of test articles were then sealed into a moisture barrier package (aluminum mylar pouch) that also contained 10 g silica desiccant and 500 cc oxygen scavenger. Sets of packaged test articles were then stored at 4° C., 23° C., and 46° C. for 6 months. At various time points the preserved test articles were removed from their respective sealed mylar pouch, the cells were recovered from the test articles and the colony forming units (CFUs) were enumerated using serial dilutions and trypticase soy agar (TSA) media. The inoculated TSA plates were placed into a 35-C incubator for approximately 18 hours. The colony counts are shown below. Three replicates for each data point were collected. SD standard deviation.

TABLE 5

| Preserved test articles stored at various temperatures for 6 months | | | | | |
|---|---|---|---|---|---|
| Time Point | Storage Temperature | Log 10 CFU/Test Article | Average Log 10 CFU/Test Article | SD | Log Loss from T = 0 |
| T = 0 | 4° C. | 6.33 | 6.28 | 0.21 | N/A |
| | | 6.46 | | | |
| | | 6.05 | | | |
| T = 2 weeks | 4° C. | 6.38 | 6.39 | 0.03 | −0.11 |
| | | 6.42 | | | |
| | | 6.38 | | | |
| T = 1 month | 4° C. | 6.59 | 6.54 | 0.07 | −0.26 |
| | | 6.57 | | | |
| | | 6.46 | | | |
| | 23° C. | 6.51 | 6.49 | 0.03 | −0.22 |
| | | 6.51 | | | |
| | | 6.46 | | | |
| | 35° C. | 5.74 | 5.87 | 0.11 | 0.41 |
| | | 5.94 | | | |
| | | 5.92 | | | |

TABLE 5-continued

Preserved test articles stored at various temperatures for 6 months

| Time Point | Storage Temperature | Log 10 CFU/Test Article | Average Log 10 CFU/Test Article | SD | Log Loss from T = 0 |
|---|---|---|---|---|---|
| T = 2 months | 4° C. | 6.14 | 6.27 | 0.13 | 0.01 |
| | | 6.40 | | | |
| | | 6.27 | | | |
| T = 3 months | 4° C. | 6.51 | 6.55 | 0.04 | −0.27 |
| | | 6.59 | | | |
| | | 6.54 | | | |
| | 23° C. | 6.56 | 6.47 | 0.14 | −0.19 |
| | | 6.54 | | | |
| | | 6.30 | | | |
| | 35° C. | 6.24 | 6.05 | 0.33 | 0.22 |
| | | 6.24 | | | |
| | | 5.68 | | | |
| T = 6 months | 4° C. | 5.83 | 5.80 | 0.10 | 0.48 |
| | | 5.89 | | | |
| | | 5.69 | | | |
| | 23° C. | 5.33 | 5.68 | 0.35 | 0.60 |
| | | 5.70 | | | |
| | | 6.02 | | | |
| | 35° C. | 3.94 | 3.48 | 0.43 | 2.80 |
| | | 3.40 | | | |
| | | 3.10 | | | |

These results show that preserved test articles surprisingly had very little loss of viability at refrigeration temperature (4° C.) and room temperature (23° C.) through 6 months, and at a highly elevated temperature (35° C.) for at least 3 months.

Example 4—Evaluation of Sanitizer Testing Performance of Preserved Antimicrobial Test Articles Compared to Freshly-Prepared Antimicrobial Test Articles The performance of preserved *Staphylococcus aureus* antimicrobial test articles in sanitizer efficacy testing was compared to freshly-prepared antimicrobial test articles. Three levels (low, moderate, high) for two exemplary antimicrobial products (NaOCl and CAVICIDE™) were evaluated. The testing was conducted by two analysts across multiple test dates.

Preserved antimicrobial test articles were prepared by the following method. *Staphylococcus aureus* (ATCC® 6538™) was grown in nutrient broth for 48 hours at 35° C. The cells were then concentrated in a stabilizing mixture comprising 2% w/v sucrose and nutrient broth. 10 µL of the cell solution comprising the stabilizing mixture was coated onto sterile 1"×1" glass slides to create test articles. The test articles were then air dried at room temperature (approximately 23° C.) for approximately 40 minutes or until the coated cell solution was substantially evaporated. Each set of test articles were then sealed into a moisture barrier package (aluminum mylar pouch) that also contained 10 g silica desiccant and 500 cc oxygen scavenger. On each respective test day the preserved antimicrobial test articles were removed from their sealed mylar pouch and utilized in antimicrobial testing per ASTM E1153—which included placing the preserved test article in a sterile vessel, contacting the preserved test article with the test sample without rehydrating the preserved antimicrobial article and without detaching the layer comprising the viable microbial material from the substrate prior to contact with the test sample, maintaining contact between the antimicrobial test article and the test sample for a predetermined test contact time and quantifying the log reduction due to the test sample. Freshly-prepared antimicrobial test articles were prepared and tested according to ASTM E1153. Results for both preserved and freshly-prepared test articles were analyzed/calculated according to ASTM E1153. Cav_1:120=CAVICIDE™ diluted to 1:120. Cav_1:30=CAVICIDE™ diluted to 1:30. Cav_RTU=CAVICIDE™ ready-to-use concentration.

TABLE 6

Positive control descriptive statistics comparing freshly-prepared test articles and preserved test articles

| Variable | N | Mean | SE Mean | StDev | Min. | Q1 | Median | Q3 | Max |
|---|---|---|---|---|---|---|---|---|---|
| Freshly-prepared | 48 | 6.54 | 0.08 | 0.55 | 5.35 | 6.17 | 6.59 | 6.92 | 7.70 |
| Preserved | 39 | 6.70 | 0.05 | 0.32 | 5.81 | 6.54 | 6.70 | 6.95 | 7.18 |

Figure 5:
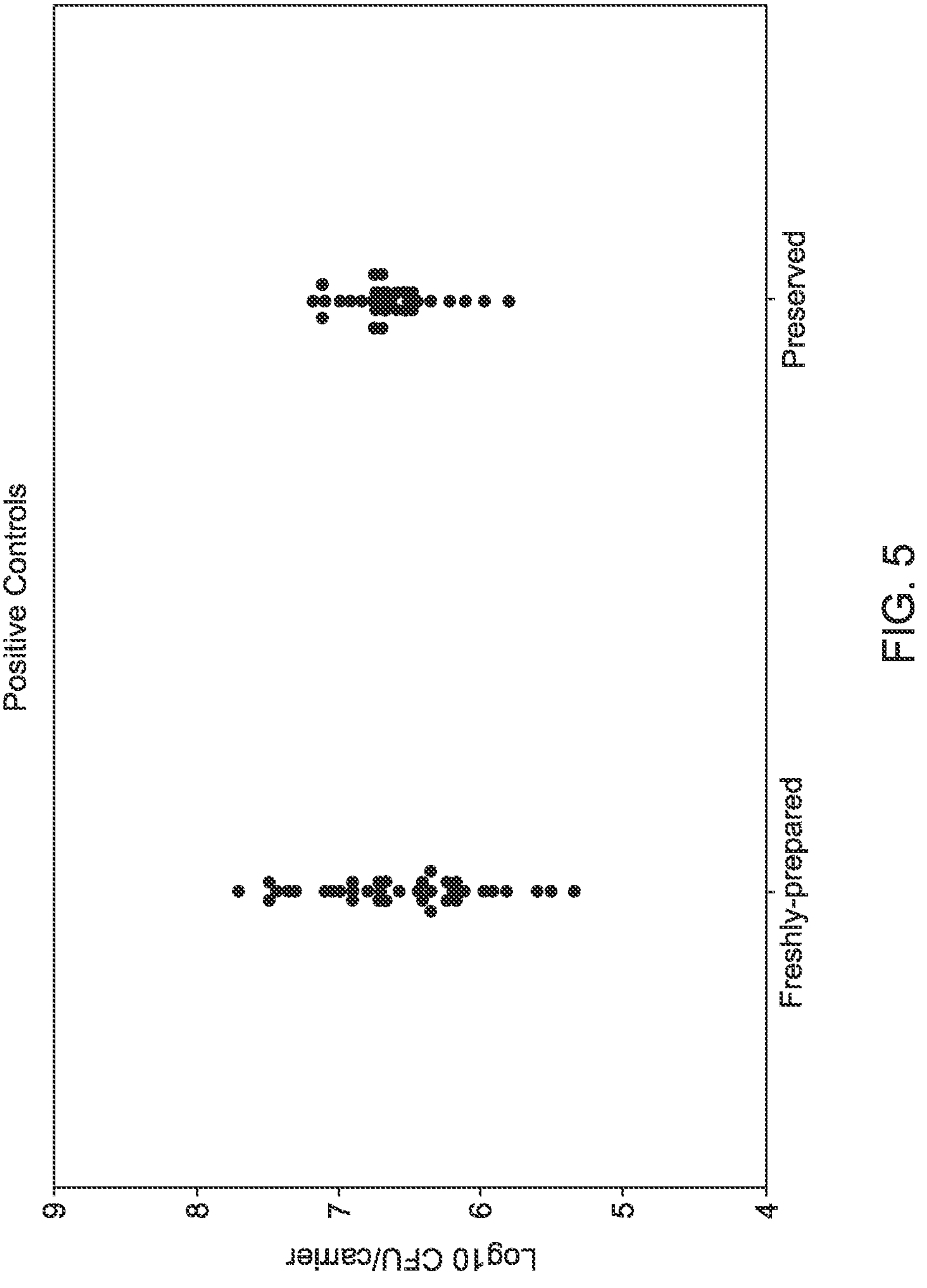
FIG. 5 is a chart of the positive controls for Example 4.

A chart of the positive controls for Example 4 is depicted in FIG. 5 (Freshly-prepared=freshly-prepared test articles; Preserved=preserved test articles).

The 95% confidence interval for the mean value (log 10 CFU/test article) of preserved test article positive controls minus the mean value (log 10 CFU/test article) for freshly-prepared test article positive controls was (−0.002, 0.314). This is well within the art's accepted lower equivalence limit and upper equivalence limit of (−0.5, 0.5). These results show that preserved test article positive controls were statistically equivalent to freshly-prepared test article positive controls. The preserved test article positive controls had a lower standard deviation than freshly-prepared test article positive controls.

TABLE 7

Testing data for preserved and freshly-prepared test articles

| Test Day | Formulation | Test Sample | Log10 CFU/Test Article | Log Reduction |
|---|---|---|---|---|
| 11 | Freshly-prepared | Cav_1:120 | 6.30 | 1.18 |
| 11 | Freshly-prepared | Cav_1:120 | 5.89 | 1.59 |
| 11 | Freshly-prepared | Cav_1:120 | 5.10 | 2.38 |
| 11 | Freshly-prepared | Cav_1:120 | 5.24 | 2.23 |
| 12 | Freshly-prepared | Cav_1:120 | 5.63 | 0.63 |
| 12 | Freshly-prepared | Cav_1:120 | 4.40 | 1.86 |
| 12 | Freshly-prepared | Cav_1:120 | 6.50 | −0.24 |
| 12 | Freshly-prepared | Cav_1:120 | 4.24 | 2.02 |
| 12 | Freshly-prepared | Cav_1:120 | 5.18 | 1.08 |
| 13 | Freshly-prepared | Cav_1:120 | 5.24 | 0.97 |
| 13 | Freshly-prepared | Cav_1:120 | 5.83 | 0.38 |
| 13 | Freshly-prepared | Cav_1:120 | 5.60 | 0.61 |
| 13 | Freshly-prepared | Cav_1:120 | 6.65 | −0.44 |
| 13 | Freshly-prepared | Cav_1:120 | 5.88 | 0.34 |
| 1 | Freshly-prepared | Cav_1:30 | 1.10 | 5.50 |
| 1 | Freshly-prepared | Cav_1:30 | 1.10 | 5.50 |
| 1 | Freshly-prepared | Cav_1:30 | 1.10 | 5.50 |
| 1 | Freshly-prepared | Cav_1:30 | 1.10 | 5.50 |
| 1 | Freshly-prepared | Cav_1:30 | 1.40 | 5.20 |
| 12 | Freshly-prepared | Cav_1:60 | 3.18 | 3.08 |
| 12 | Freshly-prepared | Cav_1:60 | 2.70 | 3.56 |
| 12 | Freshly-prepared | Cav_1:60 | 4.22 | 2.04 |
| 12 | Freshly-prepared | Cav_1:60 | 2.10 | 4.16 |
| 12 | Freshly-prepared | Cav_1:60 | 5.10 | 1.16 |
| 13 | Freshly-prepared | Cav_1:60 | 5.48 | 0.74 |
| 13 | Freshly-prepared | Cav_1:60 | 5.72 | 0.49 |
| 13 | Freshly-prepared | Cav_1:60 | 5.30 | 0.91 |
| 13 | Freshly-prepared | Cav_1:60 | 5.72 | 0.49 |
| 13 | Freshly-prepared | Cav_1:60 | 5.86 | 0.35 |
| 1 | Freshly-prepared | Cav_RTU | 1.10 | 5.50 |
| 1 | Freshly-prepared | Cav_RTU | 1.10 | 5.50 |
| 1 | Freshly-prepared | Cav_RTU | 1.10 | 5.50 |

TABLE 7-continued

Testing data for preserved and freshly-prepared test articles

| Test Day | Formulation | Test Sample | Log10 CFU/Test Article | Log Reduction |
|---|---|---|---|---|
| 1 | Freshly-prepared | Cav_RTU | 1.10 | 5.50 |
| 1 | Freshly-prepared | Cav_RTU | 1.10 | 5.50 |
| 1 | Freshly-prepared | NaOCI 10 ppm | 6.95 | 0.30 |
| 1 | Freshly-prepared | NaOCI 10 ppm | 7.08 | 0.17 |
| 1 | Freshly-prepared | NaOCI 10 ppm | 6.95 | 0.30 |
| 1 | Freshly-prepared | NaOCI 10 ppm | 6.46 | 0.79 |
| 1 | Freshly-prepared | NaOCI 10 ppm | 7.21 | 0.04 |
| 1 | Freshly-prepared | NaOCI 500 ppm | 4.14 | 3.11 |
| 1 | Freshly-prepared | NaOCI 500 ppm | 1.10 | 6.15 |
| 1 | Freshly-prepared | NaOCI 500 ppm | 1.10 | 6.15 |
| 1 | Freshly-prepared | NaOCI 500 ppm | 1.10 | 6.15 |
| 3 | Freshly-prepared | NaOCI 50 ppm | 1.10 | 5.10 |
| 3 | Freshly-prepared | NaOCI 50 ppm | 2.93 | 3.27 |
| 3 | Freshly-prepared | NaOCI 50 ppm | 5.63 | 0.57 |
| 3 | Freshly-prepared | NaOCI 50 ppm | 1.10 | 5.10 |
| 3 | Freshly-prepared | NaOCI 50 ppm | 1.10 | 5.10 |
| 4 | Freshly-prepared | NaOCI 50 ppm | 6.13 | 0.49 |
| 4 | Freshly-prepared | NaOCI 50 ppm | 6.28 | 0.34 |
| 4 | Freshly-prepared | NaOCI 50 ppm | 6.09 | 0.53 |
| 4 | Freshly-prepared | NaOCI 50 ppm | 5.57 | 1.05 |
| 4 | Freshly-prepared | NaOCI 50 ppm | 1.40 | 5.22 |
| 5 | Freshly-prepared | NaOCI 50 ppm | 6.48 | −0.13 |
| 5 | Freshly-prepared | NaOCI 50 ppm | 5.92 | 0.43 |
| 5 | Freshly-prepared | NaOCI 50 ppm | 6.51 | −0.16 |
| 5 | Freshly-prepared | NaOCI 50 ppm | 6.40 | −0.05 |
| 6 | Freshly-prepared | NaOCI 50 ppm | 1.70 | 4.65 |
| 6 | Freshly-prepared | NaOCI 50 ppm | 6.48 | −0.13 |
| 6 | Freshly-prepared | NaOCI 50 ppm | 5.92 | 0.43 |
| 6 | Freshly-prepared | NaOCI 50 ppm | 6.51 | −0.16 |
| 6 | Freshly-prepared | NaOCI 50 ppm | 6.40 | −0.05 |
| 8 | Freshly-prepared | NaOCI 50 ppm | 5.86 | −0.30 |
| 8 | Freshly-prepared | NaOCI 50 ppm | 3.44 | 2.13 |
| 8 | Freshly-prepared | NaOCI 50 ppm | 4.63 | 0.94 |
| 8 | Freshly-prepared | NaOCI 50 ppm | 5.15 | 0.41 |
| 8 | Freshly-prepared | NaOCI 50 ppm | 1.10 | 4.47 |
| 9 | Freshly-prepared | NaOCI 50 ppm | 4.94 | 1.09 |
| 9 | Freshly-prepared | NaOCI 50 ppm | 6.48 | −0.45 |
| 9 | Freshly-prepared | NaOCI 50 ppm | 2.76 | 3.27 |
| 9 | Freshly-prepared | NaOCI 50 ppm | 3.20 | 2.83 |
| 9 | Freshly-prepared | NaOCI 50 ppm | 6.24 | −0.21 |
| 14 | Preserved | Cav_1:120 | 4.88 | 1.79 |
| 14 | Preserved | Cav_1:120 | 5.92 | 0.75 |
| 14 | Preserved | Cav_1:120 | 5.98 | 0.69 |
| 14 | Preserved | Cav_1:120 | 6.21 | 0.45 |
| 14 | Preserved | Cav_1:120 | 5.18 | 1.49 |
| 2 | Preserved | Cav_1:30 | 1.10 | 6.02 |
| 2 | Preserved | Cav_1:30 | 4.34 | 2.77 |
| 2 | Preserved | Cav_1:30 | 3.10 | 4.02 |
| 2 | Preserved | Cav_1:30 | 1.10 | 6.02 |
| 2 | Preserved | Cav_1:30 | 2.10 | 5.02 |
| 14 | Preserved | Cav_1:60 | 5.81 | 0.85 |
| 14 | Preserved | Cav_1:60 | 4.52 | 2.15 |
| 14 | Preserved | Cav_1:60 | 5.35 | 1.31 |
| 2 | Preserved | Cav_RTU | 1.10 | 6.02 |
| 2 | Preserved | Cav_RTU | 1.10 | 6.02 |
| 2 | Preserved | Cav_RTU | 1.10 | 6.02 |
| 2 | Preserved | Cav_RTU | 1.10 | 6.02 |
| 2 | Preserved | NaOCI 10 ppm | 6.90 | 0.12 |
| 2 | Preserved | NaOCI 10 ppm | 6.95 | 0.07 |
| 2 | Preserved | NaOCI 10 ppm | 7.04 | −0.02 |
| 2 | Preserved | NaOCI 10 ppm | 6.48 | 0.55 |
| 2 | Preserved | NaOCI 10 ppm | 7.03 | −0.01 |
| 2 | Preserved | NaOCI 500 ppm | 1.10 | 5.93 |
| 2 | Preserved | NaOCI 500 ppm | 1.10 | 5.93 |
| 2 | Preserved | NaOCI 500 ppm | 1.10 | 5.93 |
| 2 | Preserved | NaOCI 500 ppm | 1.10 | 5.93 |
| 2 | Preserved | NaOCI 500 ppm | 3.19 | 3.84 |
| 3 | Preserved | NaOCI 50 ppm | 5.10 | 1.10 |
| 3 | Preserved | NaOCI 50 ppm | 5.97 | 0.23 |
| 3 | Preserved | NaOCI 50 ppm | 5.99 | 0.21 |
| 3 | Preserved | NaOCI 50 ppm | 5.95 | 0.24 |
| 3 | Preserved | NaOCI 50 ppm | 1.40 | 4.80 |
| 4 | Preserved | NaOCI 50 ppm | 1.10 | 5.78 |
| 4 | Preserved | NaOCI 50 ppm | 5.24 | 1.64 |
| 4 | Preserved | NaOCI 50 ppm | 6.51 | 0.37 |
| 4 | Preserved | NaOCI 50 ppm | 6.35 | 0.53 |
| 4 | Preserved | NaOCI 50 ppm | 5.81 | 1.07 |
| 5 | Preserved | NaOCI 50 ppm | 5.80 | 0.63 |
| 5 | Preserved | NaOCI 50 ppm | 6.78 | −0.36 |
| 5 | Preserved | NaOCI 50 ppm | 6.83 | −0.41 |
| 5 | Preserved | NaOCI 50 ppm | 6.54 | −0.12 |
| 5 | Preserved | NaOCI 50 ppm | 1.10 | 5.33 |
| 7 | Preserved | NaOCI 50 ppm | 1.10 | 5.37 |
| 7 | Preserved | NaOCI 50 ppm | 5.99 | 0.48 |
| 7 | Preserved | NaOCI 50 ppm | 1.10 | 5.37 |
| 7 | Preserved | NaOCI 50 ppm | 4.74 | 1.72 |
| 7 | Preserved | NaOCI 50 ppm | 1.10 | 5.37 |
| 10 | Preserved | NaOCI 50 ppm | 6.21 | −0.24 |
| 10 | Preserved | NaOCI 50 ppm | 1.10 | 4.87 |
| 10 | Preserved | NaOCI 50 ppm | 1.10 | 4.87 |
| 10 | Preserved | NaOCI 50 ppm | 4.74 | 1.23 |
| 10 | Preserved | NaOCI 50 ppm | 1.10 | 4.87 |

Figure 6:
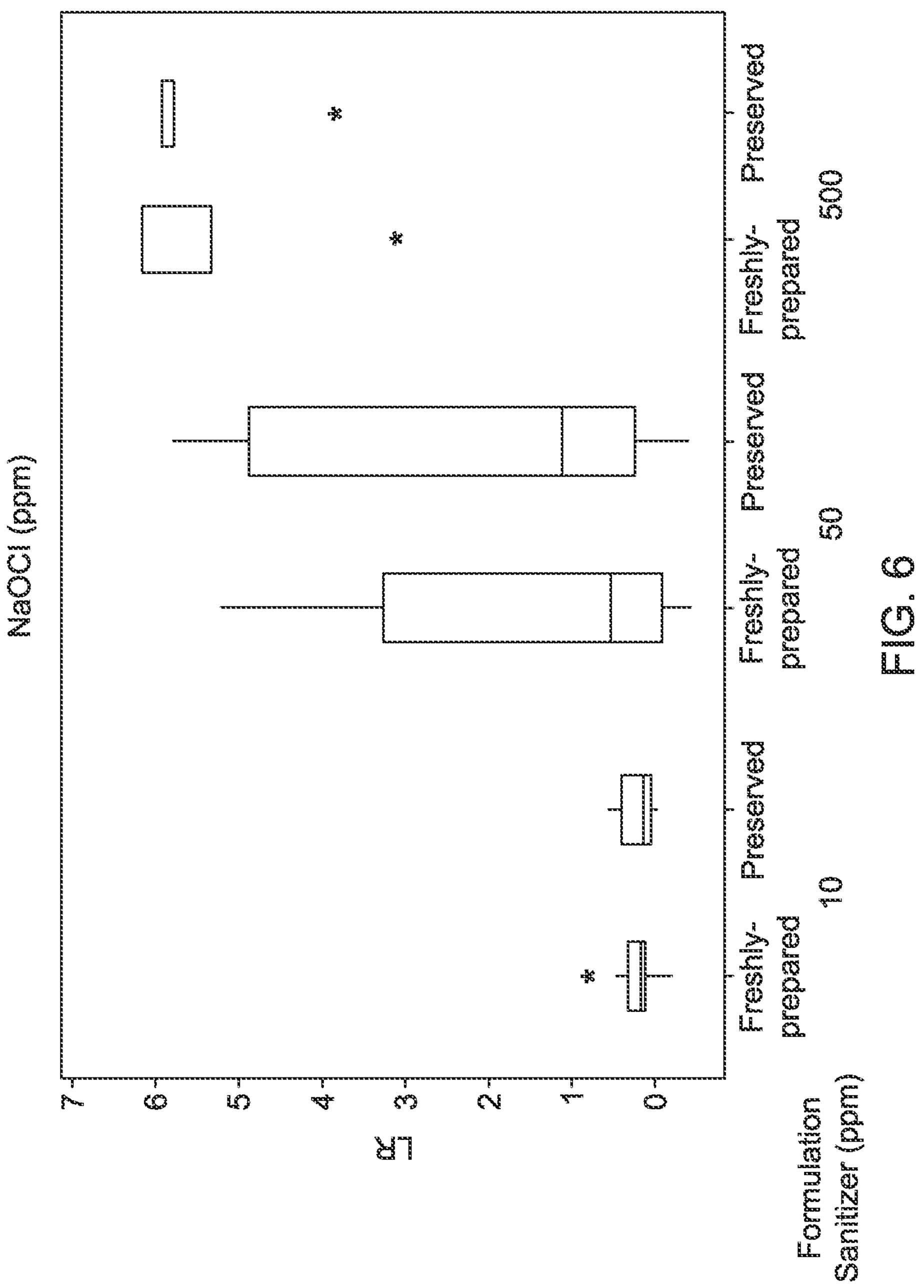
FIGS. 6-7 depict test data for Example 4.
Figure 7:
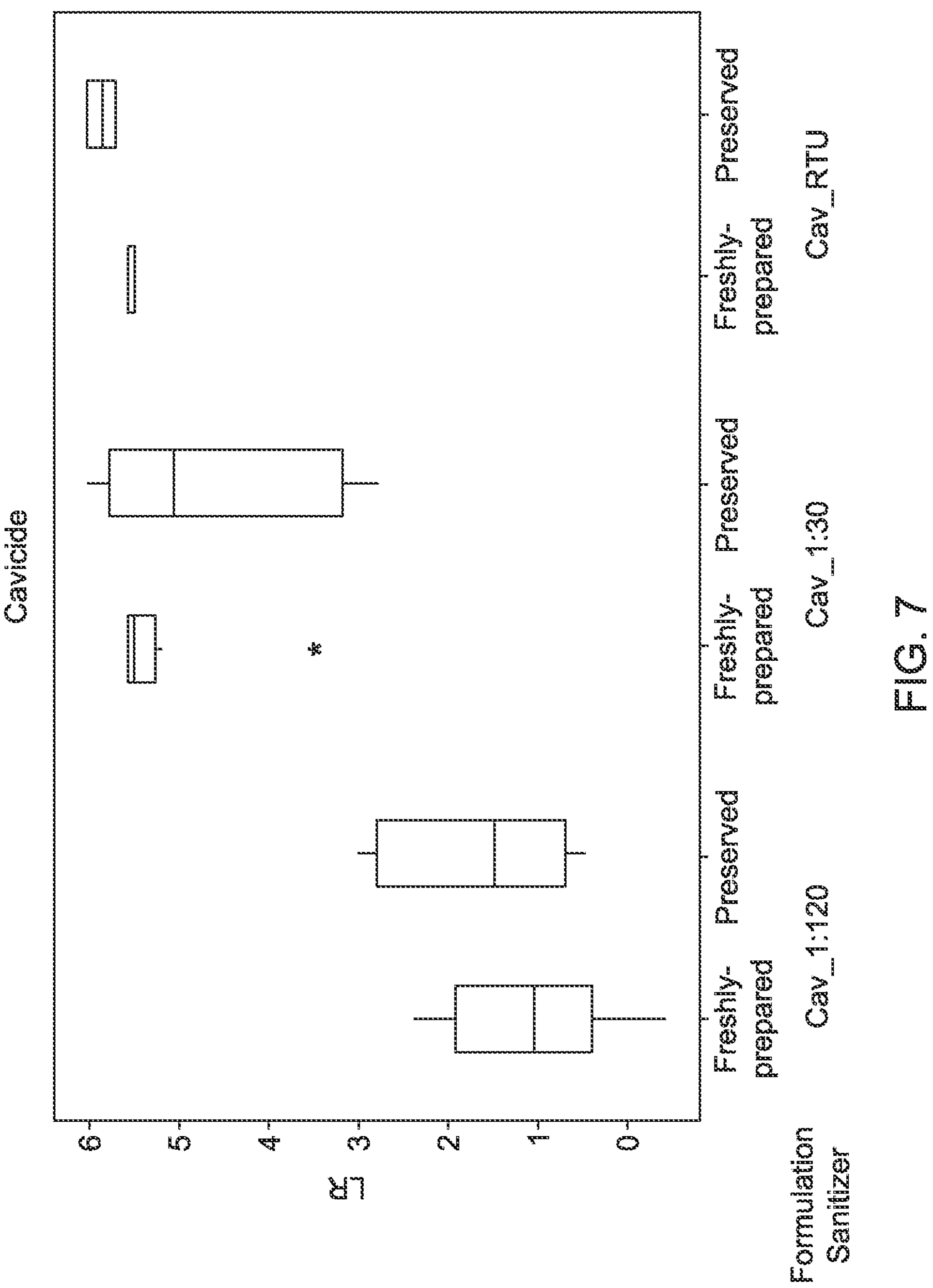

The data is depicted graphically in FIG. 6 (NaOCl test data for Example 4. LR=log reduction; Freshly-prepared=freshly-prepared test articles; Preserved=preserved test articles.) and 7 (CAVICIDE™ test data for Example 4. LR=log reduction; Freshly-prepared=freshly-prepared test articles; Preserved=preserved test articles.).

These results show that preserved test articles surprisingly were not significantly different (p-value=0.48) than freshly-prepared test articles in evaluating antimicrobial efficacy performance.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A method of evaluating the antimicrobial efficacy of a hard surface disinfectant or sanitizer, the method comprising:

removing a primary container from a secondary container, at least one of the primary container or the secondary container being impermeable to moisture and oxygen, the primary container containing a preserved antimicrobial test article, the preserved antimicrobial test article comprising:

a non-water soluble substrate, and a microbial layer attached to the substrate and comprising viable microbial material and a stabilizing mixture, wherein the viable microbial material comprises between 3.0 logs to 9.0 logs of viable microbial material and has a loss of viability of less than 1 log over at least 30 days at 4° C.;

contacting the preserved antimicrobial test article with a predetermined amount of a test substance to evaluate an antimicrobial efficacy of a hard surface disinfectant or sanitizer without rehydrating the preserved antimicrobial test article and without detaching the microbial layer from the substrate prior to contact with the test substance;

maintaining contact between the preserved antimicrobial test article and the test substance for a predetermined test contact time;

contacting the preserved antimicrobial test article and the test substance with a neutralizer after the predetermined test contact time;

agitating the preserved antimicrobial test article; and observing an indication of antimicrobial efficacy.

2. The method of claim 1, wherein observing the indication of antimicrobial efficacy includes performing a quantitative assessment.

3. The method of claim 2, wherein performing the quantitative assessment includes determining a loss of viable cells.

4. The method of claim 2, wherein performing the quantitative assessment includes utilizing a stain or a dye.

5. The method of claim 1, wherein observing the indication of antimicrobial efficacy includes performing a qualitative assessment.

6. A method of evaluating the antimicrobial efficacy of a surface disinfectant or sanitizer, the method comprising:

removing a primary container from a secondary container, at least one of the primary container or the secondary container being impermeable to moisture and oxygen, the primary container containing a preserved antimicrobial test article, the preserved antimicrobial test article comprising:

a non-water soluble substrate, and a microbial layer attached to the substrate and comprising viable microbial material and a stabilizing mixture, wherein the viable microbial material comprises between 3.0 logs to 9.0 logs of viable microbial material;

contacting the preserved antimicrobial test article with a test substance without rehydrating the preserved antimicrobial test article and without detaching the microbial layer from the substrate prior to contact with the test substance;

maintaining contact between the preserved antimicrobial test article and the test substance for a predetermined test contact time; and observing an indication of antimicrobial efficacy.

7. The method of claim 6, wherein observing the indication of antimicrobial efficacy includes performing a quantitative assessment.

8. The method of claim 7, wherein performing the quantitative assessment includes determining a loss of viable cells.

9. The method of claim 6, wherein observing the indication of antimicrobial efficacy includes performing a qualitative assessment.

10. The method of claim 1, wherein the primary container is impermeable to moisture and oxygen.

11. The method of claim 1, wherein the secondary container is impermeable to moisture and oxygen.

12. The method of claim 11, wherein the secondary container is an aluminum mylar pouch.

13. The method of claim 11, wherein the secondary container contains a desiccant therein, and the desiccant is outside of the primary container.

14. The method of claim 11, wherein the secondary container contains an oxygen scavenger therein, and the oxygen scavenger is outside of the primary container.

15. The method of claim 1, wherein the viable microbial material includes vegetative bacterial cells.

16. The method of claim 1, wherein the viable microbial material excludes spores.

17. The method of claim 1, further comprising removing the preserved antimicrobial test article from the primary container prior to contacting the preserved antimicrobial test article with the predetermined amount of the test substance.

* * * * *